United States Patent
Killpartrick et al.

(10) Patent No.: US 11,766,407 B2
(45) Date of Patent: Sep. 26, 2023

(54) POLYMERIZED WHEY PROTEIN ENCAPSULATED ANTIOXIDANT COMPOUND AND A PROCESS FOR PREPARATION OF SAME

(71) Applicant: FoodScience Corporation, Williston, VT (US)

(72) Inventors: Adam Killpartrick, Burlington, VT (US); Mingruo Guo, South Burlington, VT (US); Alyssa Humphrey Kemp, Swanton, VT (US)

(73) Assignee: FoodScience Corporation, Williston, VT (US)

(*) Notice: Subject to any disclaimer, the term of this patent is extended or adjusted under 35 U.S.C. 154(b) by 0 days.

(21) Appl. No.: 17/403,966

(22) Filed: Aug. 17, 2021

(65) Prior Publication Data

US 2022/0054422 A1    Feb. 24, 2022

Related U.S. Application Data

(60) Provisional application No. 63/067,091, filed on Aug. 18, 2020.

(51) Int. Cl.
| | |
|---|---|
| A61K 9/50 | (2006.01) |
| A61K 31/404 | (2006.01) |
| A61K 38/06 | (2006.01) |
| A61K 31/122 | (2006.01) |

(52) U.S. Cl.
CPC ......... *A61K 9/5052* (2013.01); *A61K 9/5089* (2013.01); *A61K 31/122* (2013.01); *A61K 31/404* (2013.01); *A61K 38/063* (2013.01)

(58) Field of Classification Search
CPC .. A61K 9/5052; A61K 9/5089; A61K 31/122; A61K 31/404; A61K 38/063
See application file for complete search history.

(56) References Cited

FOREIGN PATENT DOCUMENTS

WO    2009070012 A1    6/2009

OTHER PUBLICATIONS

Bule, M.V. et al., "Microencapsulation of ubiquinone-10 in carbohydrate matrices for improved stability," Carbohydrate Polymers, vol. 82, Issue 4, 2010, pp. 1290-1296.
Lu, SC "Glutathione synthesis". Biochimica et Biophysica Acta (BBA)—General Subjects (May 2013) vol. 1830 (5): pp. 3143-3153.
Wang, C. et al. "Whey Protein Functional Properties and Applications in Food Formulation," Whey Protein Production, Chemistry, Functionality, and Applications, First Edition, Edited by Mingruo Guo, Chap. 7, pp. 157-204 (2019, John Wiley & Sons Ltd, Chichester, United Kingdom).
Halprin, K.M. et al., "The measurement of glutathione in human epidermis using glutathione reductase". The Journal of Investigative Dermatology (1967) 48 (2): 149-52.
Khan, A. et al., "Physicochemical and Microstructural Properties of Polymerized Whey Protein Encapsulated 3,3'-Diindolylmethane Nanoparticles," Molecules (2019) 24:702, 16 pages.
Pastore, A. et al. "Determination of Blood Total, Reduced, and Oxidized Glutathione in Pediatric Subjects". Clinical Chemistry (Aug. 2001) 47 (8): 1467-9.
Wu, G. et al. "Glutathione Metabolism and its Implications for Health," Journal of Nutrition (2004) 134 (3): 489-92.
Zhang, S. et al., "Polymerized Whey Protein Concentrate-Based Glutathione Delivery System: Physicochemical Characterization, Bioavailability and Sub-Chronic Toxicity Evaluation," Molecules (2021) 26:1824, 13 pages.
Reed, G.A. et al., "Single-Dose Pharmacokinetics and Tolerability of Absorption-Enhanced 3,3'-Diindolylmethane in Healthy Subjects," Cancer Epidemiol. Biomarkers Prev. (2008) 17(10): 2619-2624.

*Primary Examiner* — Robert A Wax
*Assistant Examiner* — Olga V. Tcherkasskaya
(74) *Attorney, Agent, or Firm* — Amin Talati Wasserman LLP; George M. Carrera, Jr.

(57) ABSTRACT

A process is provided for encapsulating glutathione (GSH), 3,3'-diindolylmethane (DIM), coenzyme-Q10 (CoQ10), and other hydrophobic antioxidant compounds by using whey proteins which may be polymerized in a particular manner. Further, compositions comprising polymerized whey protein (PWP) encapsulated glutathione, polymerized whey protein (PWP) encapsulated CoQ10, and polymerized whey protein (PWP) encapsulated DIM are provided.

5 Claims, 31 Drawing Sheets

POLYMERIZED WHEY PROTEIN ENCAPSULATED ANTIOXIDANT COMPOUND AND A PROCESS FOR PREPARATION OF SAME

This application claims the benefit of U.S. Provisional application No. 63/067,091, filed on Aug. 18, 2020, which is hereby incorporated by reference herein.

TECHNICAL FIELD

The present invention relates to a process for encapsulating glutathione (GSH), 3,3'-diindolylmethane (DIM), CoEnzyme Q10 (CoQ10), and other hydrophobic antioxidant compounds by using whey proteins which may be polymerized in a particular manner. Herein are described compositions comprising polymerized whey protein encapsulated glutathione, DIM, CoEnzyme Q10, and the like.

BACKGROUND

Glutathione (GSH) is an antioxidant found in plants, animals, fungi, and some bacteria. Glutathione is the most abundant thiol in animal cells, ranging from 0.5 to 10 mM. It is present both in the cytosol and the organelles (Guoyao Wu, Yun-Zhong Fang, Sheng Yang, Joanne R. Lupton, Nancy D. Turner. "Glutathione Metabolism and its Implications for Health," Journal of Nutrition (2004) 134 (3): 489-92).

Glutathione exists in reduced (GSH) and oxidized (GSSG) states. The ratio of reduced glutathione to oxidized glutathione within cells is a measure of cellular oxidative stress where increased GSSG to GSH ratio is indicative of greater oxidative stress (A. Pastore, et al., "Determination of blood total, reduced, and oxidized glutathione in pediatric subjects". Clinical Chemistry (August 2001) 47 (8): 1467-9; SC Lu. "Glutathione synthesis". Biochimica et Biophysica Acta (BBA)—General Subjects (May 2013) 1830 (5): 3143-53). In healthy cells and tissues, more than 90% of the total glutathione pool is in the reduced form (GSH), with the remainder in the disulfide form (GSSG); (K. M. Halprin, A. Ohkawara "The measurement of glutathione in human epidermis using glutathione reductase". The Journal of Investigative Dermatology (1967) 48 (2): 149-52).

GSH protects cells by neutralizing (i.e., reducing) reactive oxygen species. This conversion is illustrated by the reduction of peroxides:

2GSH+R2O2→GSSG+2ROH(R=H,alkyl)

Also, free radicals may be quenched in vivo:

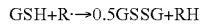

GSH+R·→0.5GSSG+RH

In addition, glutathione plays a key role in cellular regulation and metabolism. With respect to these key metabolic and cellular roles, it would be advantageous to provide glutathione in a stable and bioavailable composition. Glutathione suffers from a lack of oral bioavailability in the digestive tract. Previous encapsulation technologies have been developed, predominately using lipid encapsulation (such as lecithin) in conjunction with synthetic chemicals, such as polysorbate 80, in order to increase absorption of difficult to absorb compounds, but the application of whey protein or polymerized whey protein has not, until now, been applied in this way. Therefore, a safe, synthetic chemical free option is needed to increase bioavailability.

If a way could be found to improve stability and decrease degradation of glutathione in a composition for delivery to a mammal, in particular a human subject, this would provide a useful contribution to the art. Further, if a way could be found to optimize absorption of glutathione and utilization by the body, e.g. increasing bioavailability, this would provide a further useful contribution to the art Regarding encapsulation of nutrients, certain film-forming compounds and surfactants are useful, for example, polyvinylpyrrolidone, polyoxyethylene stearate, sodium cholate, deoxycholate and taurocholate phosphatidyl choline, dioleoyl phosphatidyl choline, phosphatidylglycerol, dioleoylphosphatidylglycerol, dimyristoylphosphatidylcholine, dipalmitoylphosphatidylcholine, phosphatidylethanolamine, phosphatidylserine, sphingomyelin, methylcellulose, hydroxypropyl methylcellulose, hydroxyethylcellulose, hydroxypropylethylcellulose, one or more of which may be blended with lecithin.

3,3'-diindolylmethane ("DIM") is an active metabolite of indole-3-carbinol derived from cruciferous vegetables and exhibits a broad spectrum of anticancer properties. The stability of DIM is a major challenge in the pharmaceutical industry. Moreover, DIM has poor oral bioavailability due to its low solubility and high lipophilicity. Encapsulation by whey protein is known in order to develop nanoparticles with controlled size and properties, which process may provide for the protection, preservation, and delivery of sensitive compounds such as aroma or nutraceuticals.

Certain methods are known for encapsulating 3,3'-diindolylmethane ("DIM") and like species using ultrasound. See, A. Khan, et al., "Physicochemical and Microstructural Properties of Polymerized Whey Protein Encapsulated 3,3'-Diindolylmethane Nanoparticles," Molecules (2019) 24:702.

If a way could be found to improve the encapsulation process to provide, for example, a polymerized whey protein encapsulated DIM having better stability, solubility and other improved properties such as oral bioavailability, this would provide a contribution to the chemical and formulation arts.

SUMMARY OF THE INVENTION

A composition is described including polymerized whey protein encapsulating glutathione.

A process is described for making polymerized whey protein microencapsulated glutathione, comprising the steps of: dissolving whey protein concentrate powder in water at about 8-12% w/v to provide an aqueous solution; heating the whey protein concentrate solution to at least 80° C. for about 15-25 minutes to provide a polymerized whey protein solution; adding an antioxidant compound to the polymerized whey protein solution during the cooling process; stirring with a homogenizer or shear mixer to provide a clear homogeneous solution; and isolating polymerized whey protein microencapsulated antioxidant compound, for example, by freeze-drying or spray-drying to provide a powder.

Further, a process is described for making polymerized whey protein microencapsulated DIM (PWP-DIM), comprising the steps of: (a) dissolving whey protein concentrate powder in water at 10% w/v to provide an aqueous solution; (b) heating the whey protein concentrate solution to at least about 70-80° C. to provide a polymerized whey protein solution; (c) adding DIM to the polymerized whey protein solution; (d) adjusting the pH in a range from about 6.5 to about 9.0; (e) cooling the polymerized whey protein solution; (f) stirring during cooling from about 80° C. to about 45° C. to provide a clear homogeneous solution; and (g) isolating polymerized whey protein microencapsulated DIM.

One objective is to prepare a PWP-DIM having a visibly better encasement for greater protection through the digestive tract, i.e. the GI tract.

Another objective is to prepare a PWP-DIM having improved absorption in the digestive tract.

Further, a process is described for making polymerized whey protein microencapsulated antioxidant compound, comprising the steps of: (a) dissolving whey protein concentrate powder in water at 10% w/v to provide an aqueous solution; (b) heating the whey protein concentrate solution to about 70-80° C. for about 15 minutes to provide a polymerized whey protein solution; (c) adding glutathione to the polymerized whey protein solution; (d) stirring to provide a clear homogeneous solution; and (e) isolating polymerized whey protein microencapsulated glutathione, for example, by freeze-drying to provide a powder.

In one embodiment, the process for making the polymerized whey protein microencapsulated antioxidant compound is used to make polymerized whey protein microencapsulated glutathione (PWP-GSH).

In another embodiment, the process for making the polymerized whey protein microencapsulated antioxidant compound is used to make polymerized whey protein microencapsulated coenzyme-Q10 (PWP-CoQ10).

DETAILED DESCRIPTION

Figure 1:
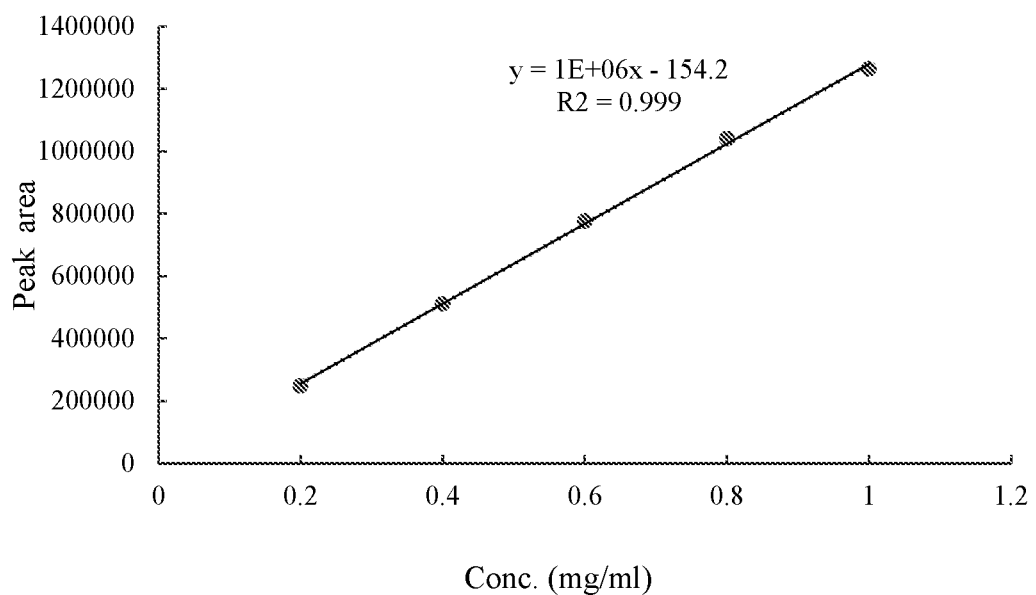
FIG. 1 depicts a standard curve for determining reduce glutathione (GSH) using HPLC. The standard curve was plotted as a function of concentrations to peak area.

In one aspect, the invention relates to microencapsulation of both fat and water soluble antioxidants with polymerized whey protein for the expressed purpose of protecting the nutrients from degradation and optimizing absorption and utilization in the body. For example, the present inventors, have contributed to and described the present method for preparation of polymerized whey protein encapsulated glutathione (PWP-GSH) in S. Zhang, et al., "Polymerized Whey Protein Concentrate-Based Glutathione Delivery System: Physicochemical Characterization, Bioavailability and Sub-Chronic Toxicity Evaluation," *Molecules* (2021) 26:1824, hereby incorporated by reference in its entirety.

In a further aspect, the invention relates to a novel process of manipulating whey protein, by adjusting temperature and pH, to allow for encapsulation of the protein around nutrients, specifically antioxidants, for protection and optimal absorption and utilization. The antioxidants that have been successfully encapsulated using the present method are glutathione, diindolylmethane, and coenzyme Q10. Current studies are underway to apply this technology for use in dietary supplements (e.g., to be tableted, encapsulated, incorporated into a ready to drink powder) and to allow antioxidants to be successfully incorporated into a variety of food and beverages to increase the food or beverage's health benefit.

The advantages of the current process is that a technically simplified and more natural process, without the use of certain chemical agents which are typically not desired by natural food or dietary supplement companies, has been realized.

In a principal embodiment, the encasement of the antioxidant compounds, and other derivatives, is more evenly uniform which allows for better protection of the active component in the digestive tract. Further, this process embodiment provides better encasement when viewed microscopically, for example using SEM or TEM.

The PWP-GSH compositions and formulations described herein demonstrated improved absorption in vivo, better pharmacokinetics, better bioavailability, and higher antioxidant capacity when compared to free GSH. The PWP-GSH compositions and formulations described herein also demonstrated improved absorption in vivo, better pharmacokinetics, and better bioavailability when compared to comparator GSH product.

Microencapsulation

Microencapsulation is a technique used for the protection of a wide range of biomolecules. See, *Whey Protein Production, Chemistry, Functionality, and Applications*, Ed. Mingruo Guo (one of the present inventors) Chap. 7, "Whey Protein Functional Properties and Applications in Food Formulation," pp. 157-204 (and references cited therein), (Wiley: Hoboken, N.J., 2019), which is incorporated by reference herein.

Formulations may be prepared as any product form suitable for use in human individuals, including reconstitutable powders, ready-to-feed liquids, parenteral (intravenous) formulations, and dilutable liquid concentrates, product forms which are all well known in the nutritional formula art. As used in the present application, the amounts of components present in formulations or compositions refer to the amounts when the formulation or composition is ready for consumption by the human individual.

Formulations or compositions can optionally be sterilized and subsequently used on a ready-to-feed basis, or can be stored as concentrates. Concentrates can be prepared by spray drying a liquid formulation prepared as above, and a formulation can be reconstituted by rehydrating the concentrate. The formulation concentrate is a stable liquid and has a suitable shelf life.

For powder embodiments of formulations or compositions comprising GSH, whey protein encapsulated GSH (WP-GSH), or polymerized whey protein encapsulated GSH (PWP-GSH), used in the methods of the present invention, reconstitution of the powder can be done with a suitable aqueous liquid, preferably water. Reconstitutable powders are typically in the form of flowable or substantially flowable particulate compositions, or at least particular compositions that can be easily scooped and measured with a spoon or similar other device, wherein the compositions can be easily reconstituted by the intended user with a suitable aqueous fluid, typically water, to form a liquid formulation or composition. In this context, "immediate" use generally means within about 48 hours, most typically within about 24 hours, preferably right after reconstitution. These powder embodiments include spray dried, agglomerated, dry mixed or other known or otherwise effective particulate form. The quantity of a nutritional powder required to produce a volume suitable for one serving can vary.

The nutritional formulas used in the methods of the present invention may be packaged and sealed in single or multi-use containers, and then stored under ambient conditions for up to about 36 months or longer, more typically from about 12 to about 24 months. For multi-use containers, these packages can be opened and then covered for repeated use by the ultimate user, provided that the covered package is then stored under ambient conditions (e.g., avoid extreme temperatures) and the contents used within about one month or so.

Compositions for oral formulations useful for delivering a dietary supplement composition comprising GSH, whey protein encapsulated GSH (WP-GSH), or polymerized whey protein encapsulated GSH (PWP-GSH), can be orally administered, for example, with an inert diluent or with an assimilable edible carrier, or it can be enclosed in hard or soft shell gelatin or hydroxypropyl methylcellulose (i.e., hypromellose) capsules, or it can be compressed into tablets, or it can be incorporated directly with the food of the diet. For oral administration, a dietary composition comprising GSH, whey protein encapsulated GSH (WP-GSH), or polymerized whey protein encapsulated GSH (PWP-GSH), may be incorporated with an excipient and used in the form of ingestible tablets, buccal tablets, troches, capsules, elixirs, suspensions, syrups, wafers, and the like. The tablets, troches, pills, capsules, and the like can also contain the following: a binder such as gum tragacanth, acacia, corn starch, or gelatin; excipients such as dicalcium phosphate, microcrystalline cellulose, and the like; a disintegrating agent such as potato starch, alginic acid, and the like; a lubricant such as magnesium stearate; and a sweetening agent such as sucrose, lactose, or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the active compound, sucrose as a sweetening agent, methyl and propylparabens as preservatives, a dye, and flavoring such as cherry or orange flavor. Oil-in-water emulsions may be better for oral use in infants because these are water-miscible, and thus their oiliness is masked. Such emulsions are well known in the pharmaceutical sciences.

Determination of GSH using HPLC

Optimum conditions for HPLC analysis:

Column: symmetry C18

Mobile phase: Water:Acetonitrile=90:10

Flow rate: 0.5 ml/min

Wavelength: 218 nm (UV detector)

Injection volume: 0.5 μL

GSH powder was dissolved in ultra-pure water to make a stock solution of 10 mg/ml. A series of standard solutions (0.2 mg/ml, 0.4 mg/ml, 0.6 mg/ml, 0.8 mg/ml, 1.0 mg/ml) were obtained by dilution of the stock solutions using ultra-pure water. GSH was determined using HPLC. The standard curve was plotted as a function of concentrations to peak area as shown in FIG. 1.

The compositions and methods described in the embodiments above may be further understood in connection with the following Examples. In addition, the following non-limiting examples are provided to illustrate the invention. However, the person skilled in the art will appreciate that it may be necessary to vary the procedures for any given embodiment of the invention, e.g., vary the order or steps of the methods.

Example 1

Whey Protein-GSH Mixture (WP-GSH)

Whey protein concentrate (WPC) solutions (10% protein, w/v) were prepared by dissolving whey protein concentrate powder in deionized water at room temperature and then stirred (700 rpm) for 2 h. The stock solution was stored at 4° C. overnight for complete hydration. Whey protein solution was warmed up to ambient temperature and then mixed with reduced-GSH at weight ratios of WPC (powder): GSH=1:1, 1:1.5 and 1:2. The mixtures were stirred for 20 min to achieve complete dissolution.

Polymerized Whey Protein Encapsulated GSH (PWP-GSH)

Whey protein concentrate (WPC) solutions (10% protein, w/v) were prepared by dissolving whey protein concentrate powder in deionized water at room temperature and then stirred (700 rpm) for 2 h. The solution was stored at 4° C. overnight for complete hydration. Whey protein solutions were returned to ambient temperature and the pH was adjusted to 7 or 8 and then heated at 80° C. for 15 min. Polymerized whey protein (PWPC) solutions were obtained by cooling the heated whey protein solutions in mixed water-ice quickly to room temperature (25±1° C.). The PWPC solutions were then mixed with GSH powder at weight ratios of PWPC:GSH=1:1, 1:1.5 and 1:2. The mixtures were mixed for 20 min to achieve complete dissolution.

Stability Experiments

All whey protein based GSH solutions were observed for stability for 20 h at room temperature. Table 1 below lists the stability of whey protein based glutathione solutions, including polymerized embodiments.

TABLE 1

| Sample | WPC/PWPC:GSH (w/w) | Time | | | |
|---|---|---|---|---|---|
| | | 0 h | 4 h | 16 h | 20 h |
| 12% WPC | 1:1 | No sediment | No sediment | No sediment | No sediment, viscous |
| | 1:1.5 | Almost no sediment | Little sediment | More sediment | More sediment |
| | 1:2 | More sediment | More sediment | Sediment increase | Sediment increase |
| 10% WPC | 1:1 | No sediment | No sediment | No sediment, running well | No sediment, running well |
| | 1:1.5 | No sediment | No sediment | No sediment | No sediment |
| | 1:2 | More sediment | More sediment | Sediment increase | Sediment increase |
| 10% PWPC (pH7) | 1:1 | No sediment | No sediment | Gel | Gel |
| | 1:1.5 | No sediment | No sediment | Gel | Gel |
| | 1:2 | More sediment | More sediment | Gel | Gel |
| 10% PWPC (pH8) | 1:1 | No sediment | No sediment | Gel | Gel |
| | 1:1.5 | No sediment | No sediment | Gel | Gel |
| | 1:2 | More sediment | More sediment | Gel | Gel |

WPC (pH 7 and pH 8) at the concentration of 12% gelled after heating.

As shown in Table 1, the PWP-GSH samples are stable to at least 4 hours.

Example 2

Pharmacokinetic Study

ICR mice, male, SPF, 3 weeks, weighing from 18 to 22 g were provided by Beijing HFK Bioscience Co., Ltd (Beijing, China). Reduced glutathione (GSH) assay kit (A006-2-1), total antioxidative capacity measurement kit (ABTS method) (A015-2-1) were purchased from Nanjing Jiancheng bioengineering institute (Nanjing, Jiangsu China).

All mice were housed in plastic lab animal cages in a ventilated room. The room was maintained at 20±2° C. and 60±10% relative humidity with a 12 h light/dark cycle. Water and commercial laboratory complete food for mice were available ad libitum. They were acclimated to this environment for 7 days before treatment. All animal experiments were approved by the Animal Welfare and Research Ethics Committee at Jilin University (Approval ID: SY201905018).

Blood collection. Before blood collection, 30 μL heparin solution was added to 1.5 mL centrifugal tubes and vortexed. The blood samples (about 0.5 mL) was collected by removing one eye of the mice. The blood was centrifuged at 6000 rpm at room temperature for 2 min. The upper plasma was transferred to a new centrifugal tube. The plasma concentration of GSH was analyzed using the GSH assay kit.

Figure 2:
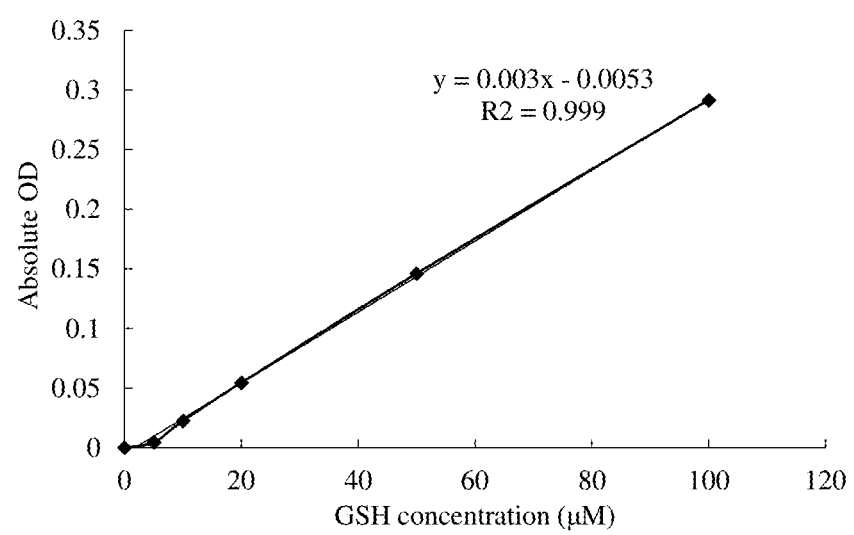
FIG. 2 depicts a standard curve for determining reduce glutathione (GSH) using an assay kit. The standard solutions were plotted as absolute OD value vs GSH concentration (μM).

GSH stock solution (1 mmol/L) was diluted to a series of standard solutions at concentrations of 0 μmol/L, 5 μmol/L, 10 μmol/L, 20 μmol/L and 100 μmol/L. The standard solutions were plotted as absolute OD value vs GSH concentration (FIG. 2).

A. The blood samples were collected after oral administration of free GSH, whey protein based GSH, whey protein, polymerized whey protein based GSH and polymerized whey protein by gavage at several time points (0, 15 min, 30 min, 1 h, 2 h and 4 h) in each group of 6 mice. The dose of the whey protein based GSH is adjusted to have an equivalent amount of 100 mg/kg of GSH. The GSH concentration in the blood samples are determined by assay kit.

Table 2 shows test groups and gavage volume.

TABLE 2

| Sample | Control | 10% WPC | 10% PWPC | 10% WPC-GSH | 10% PWPC-GSH | GSH |
|---|---|---|---|---|---|---|
| Gavage Volume | 0.3 mL saline | 0.3 mL | 0.3 mL | 0.3 mL | 0.3 mL | 0.3 mL |

Figure 3:
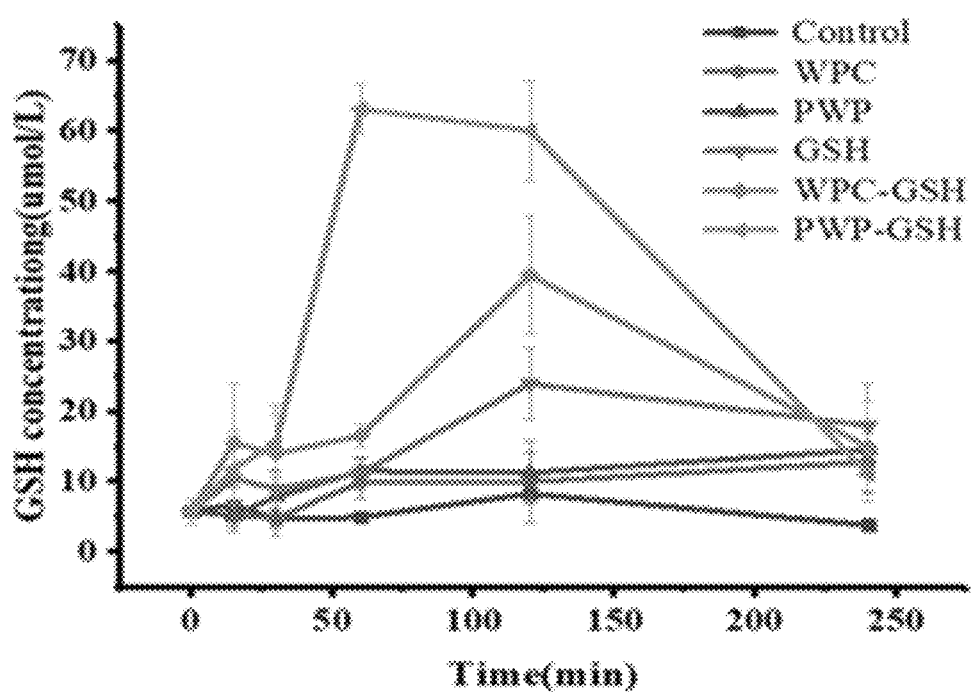
FIG. 3 depicts reduced glutathione (GSH) plasma concentration (mon) as a function of time after oral administration of test samples in mice.

As shown in FIG. 3, PWP-GSH test material provides an excellent and significant increase in concentration of GSH in plasma after oral administration.

B. Antioxidant Activity In Vivo

Figure 4:
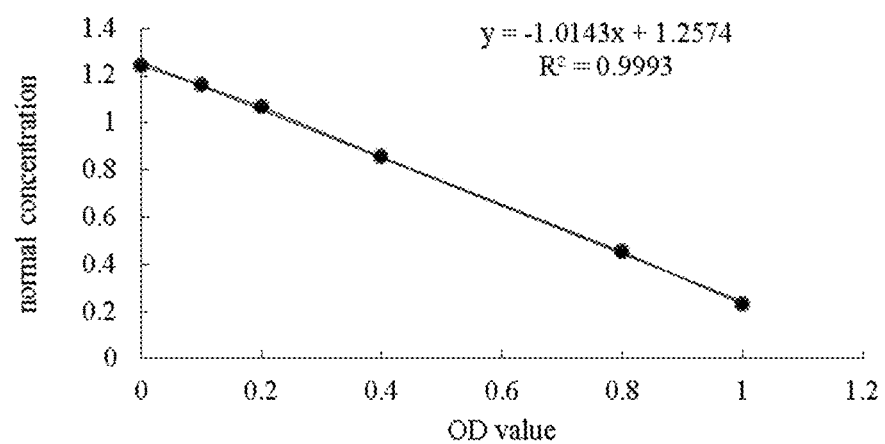
FIG. 4 depicts a standard curve for determining the antioxidant activity of plasma. The standard curve was plotted by determining the OD values of different standard samples at 0.1, 0.2, 0.4, 0.8, and 1.0 mM.

Trolox stock solution (10 mM) was diluted to 0.1, 0.2, 0.4, 0.8, 1.0 mM. The standard curve was plotted by determining the OD values of different standard samples (FIG. 4). The antioxidant activity of plasma was expressed as the fold of capacity to Trolox with the TAOC (total antioxidative capacity) of Trolox as 1.

Figure 5:
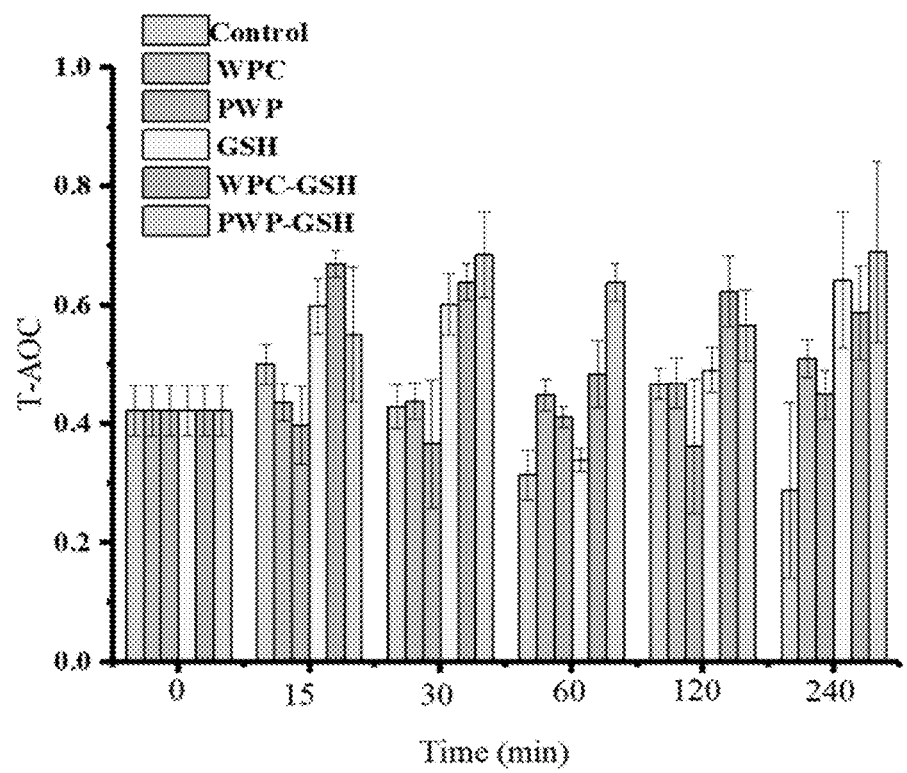
FIG. 5 depicts, in an embodiment, the in vivo antioxidant activity of plasma of mice after oral administration of free GSH, WPC/PWPC based GSH, WPC/PWPC, as measured by assay kit (ABTS method). The order of the vertical bars at individual time points, from left to right: Control, WPC, PWP, GSH, WPC-GSH, and PWP-GSH.
Figure 6A:
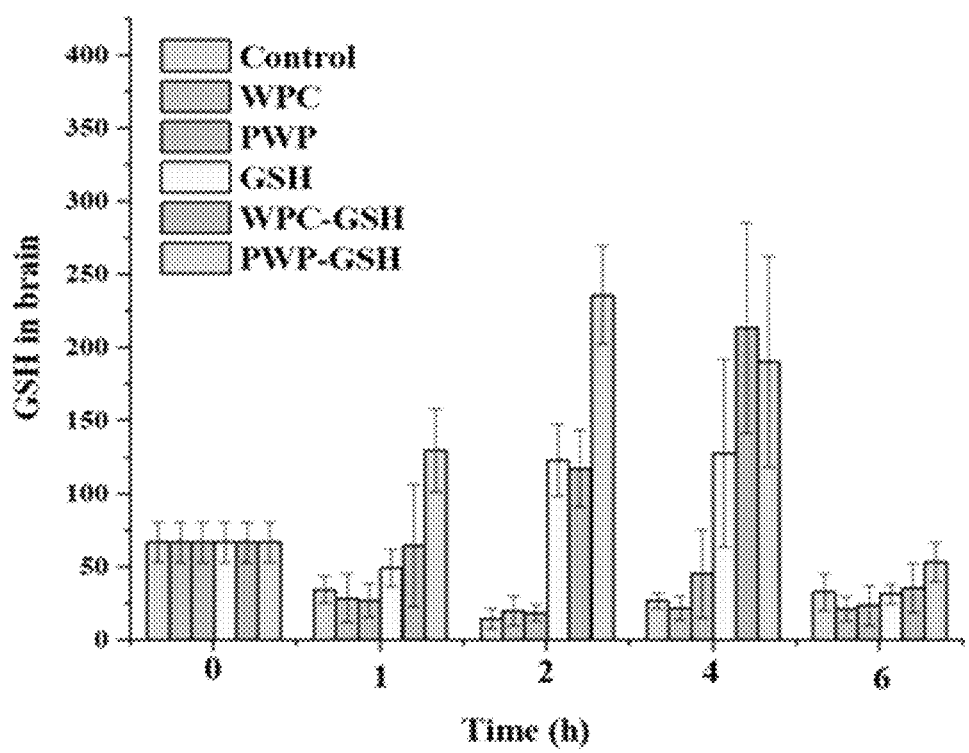
FIGS. 6A-6F depicts, in another embodiment, GSH concentration (μM) in the tissues of mice measured after oral administration of free GSH, WPC/PWPC based GSH, WPC/PWPC. The order of the vertical bars at individual time points, from left to right: Control, WPC, PWP, GSH, WPC-GSH, and PWP-GSH. Figures A-F show measurements in brain (A), heart (B), lung (C), kidney (D), liver (E), and intestine (F).
Figure 6B:
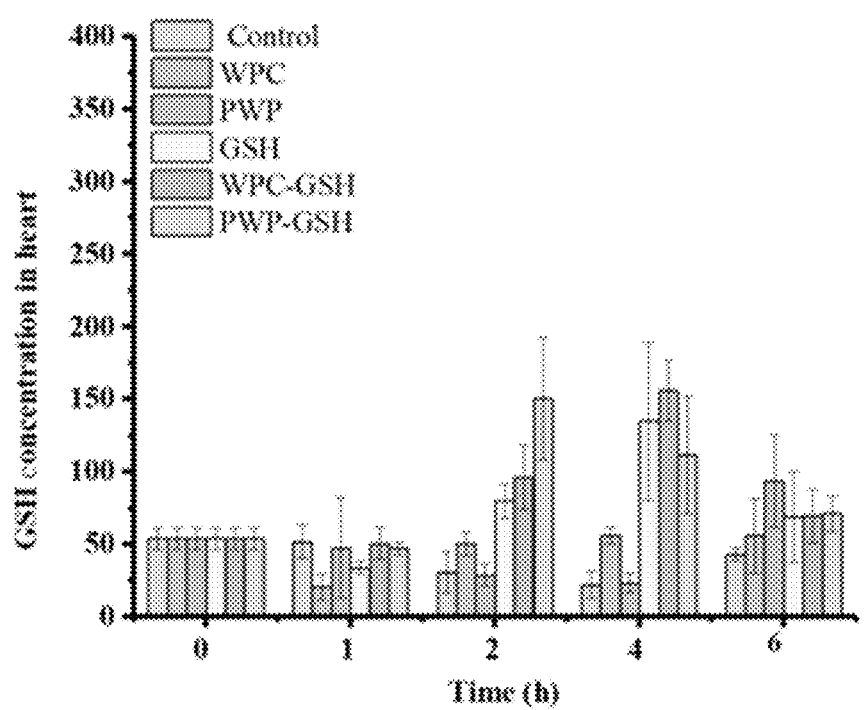
Figure 6C:
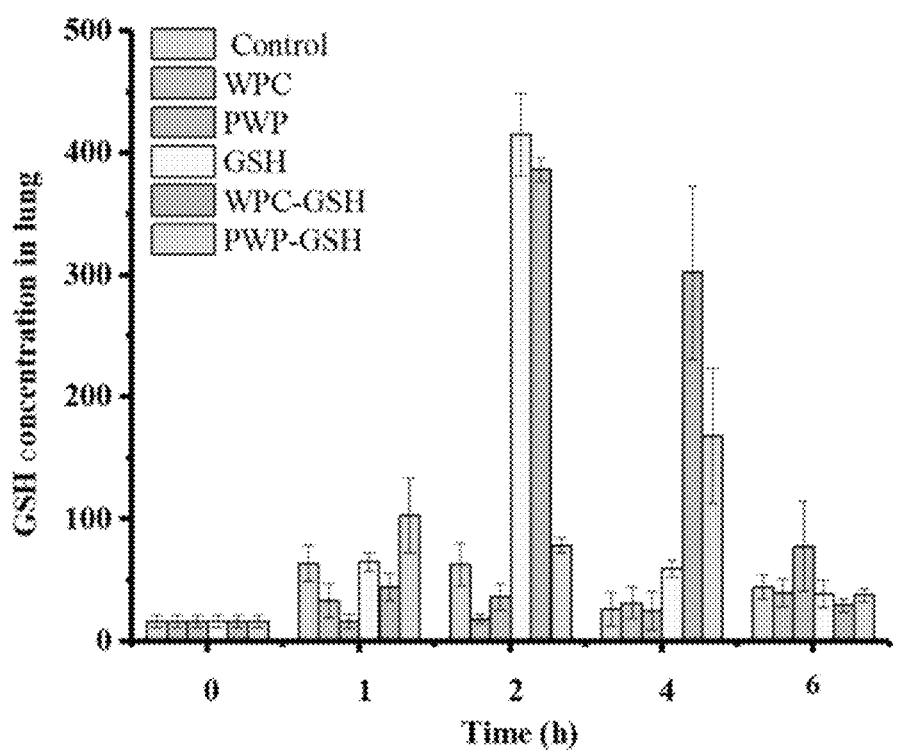
Figure 6D:
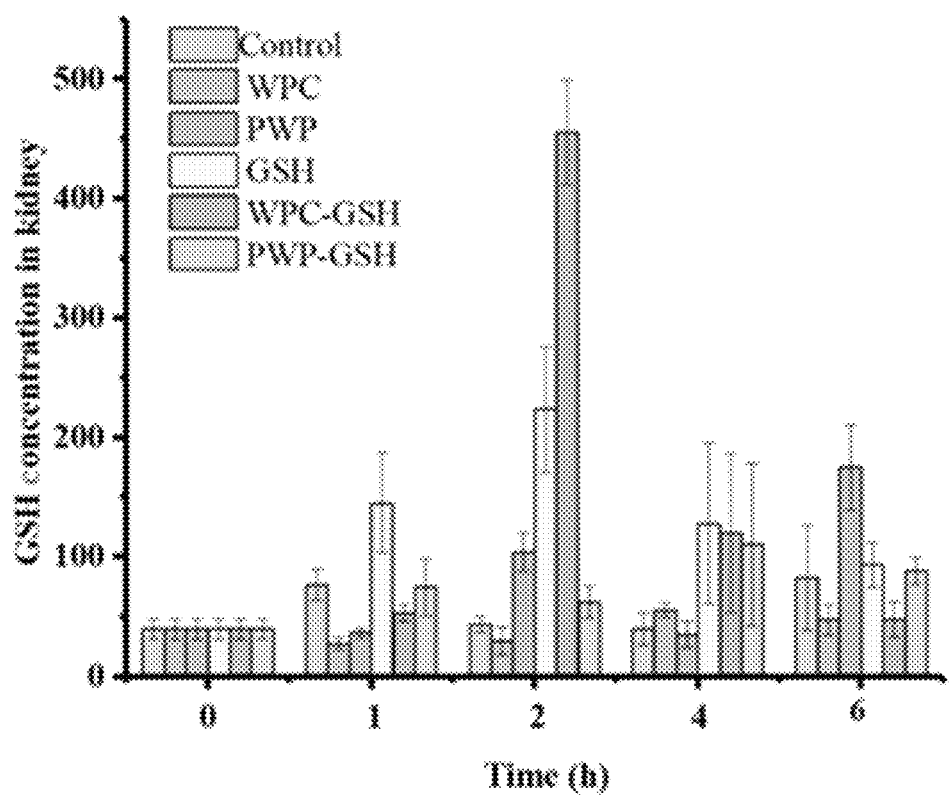
Figure 6E:
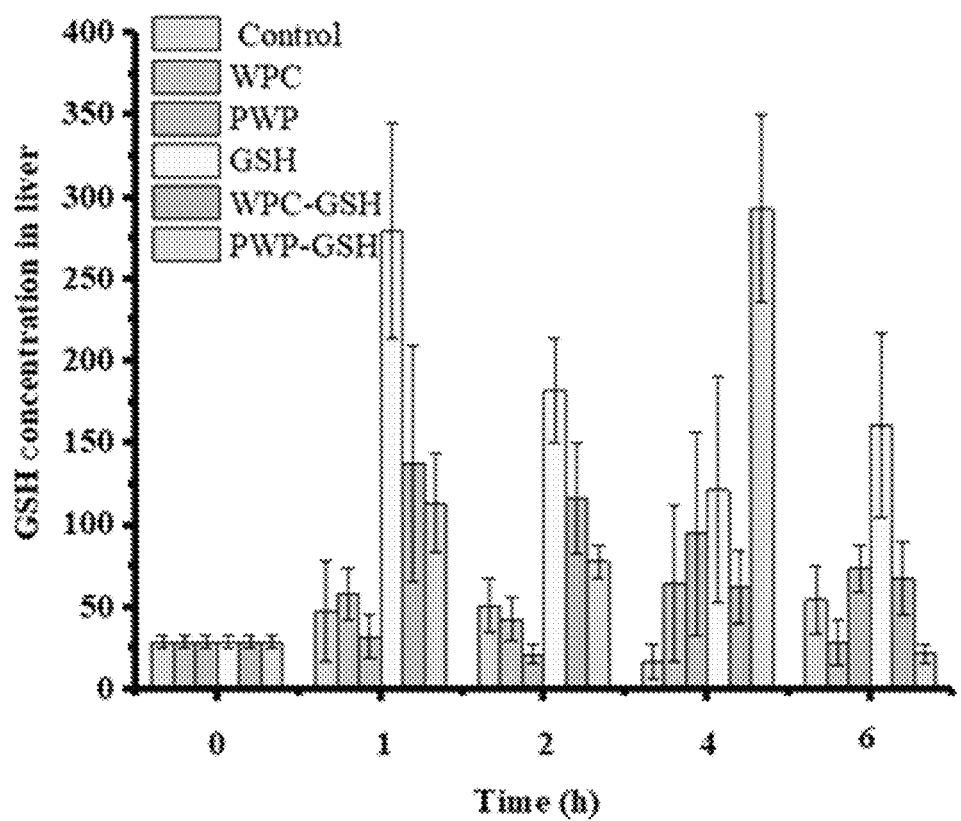
Figure 6F:
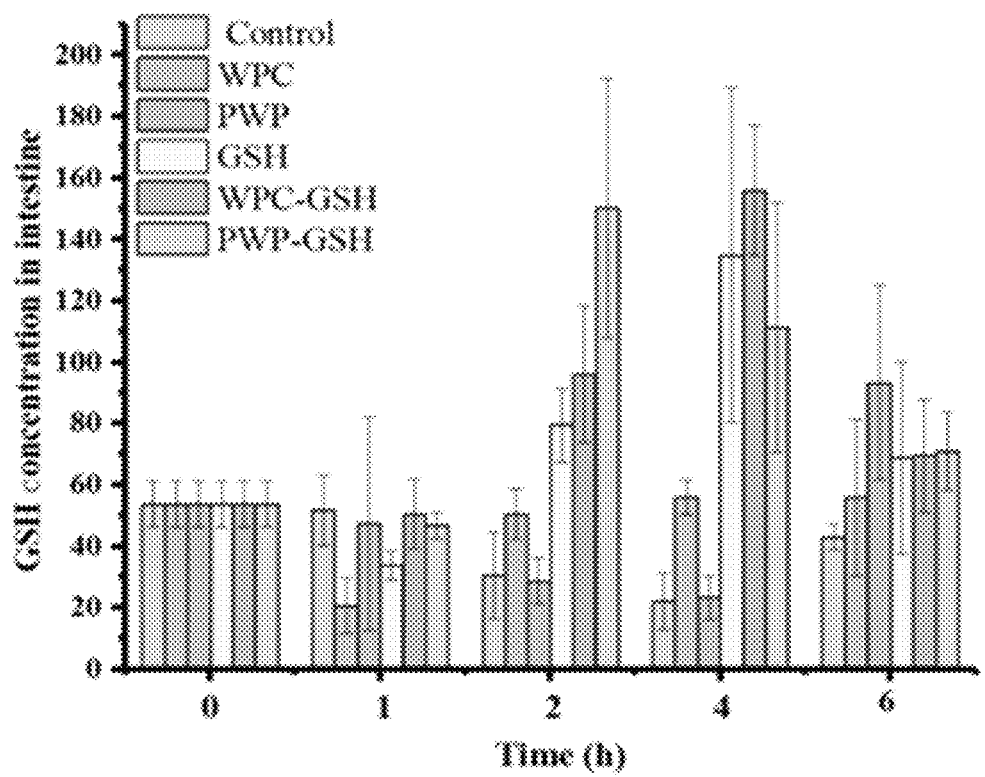

The total antioxidative capacity of all samples were also measured using the assay kit and the results are shown in FIG. 5. In vivo antioxidant activity of plasma of mice after oral administration of free GSH, WPC/PWPC based GSH, WPC/PWPC, was measured by assay kit (ABTS method).

As shown in FIG. 5, PWP-GSH sample over time exhibits the most robust antioxidant activity.

C. Tissue Distribution of GSH

To evaluate delivery efficiency of GSH to the organs, the tissue samples of brain, heart, kidney, liver, lung, and intestine were collected at 0, 1, 2, 4, and 6 h post-oral administration in each group of 6 mice. The tissues were homogenized, protein precipitated, centrifuged, and then analyzed for GSH content using the assay kit (FIGS. 6A-6F).

As shown in FIGS. 6A-6F, distribution of free GSH in various tissues was significantly greater than control. Further, distribution of GSH for the PWP-GSH group in various tissues was significantly greater than control.

D. Toxicity Study of Polymerized Whey Protein Based GSH (PWP-GSH)

Whey protein concentrates were provided by Fonterra Co-operative Group (Auckland, New Zealand). Pentobarbital sodium, formalin and absolute ethanol were provided by Beijing Works (Beijing, China). SD rats at week 3 were provided by Beijing HFK Bioscience Co., Ltd (Beijing, China).

Diet Formulations

Polymerized whey protein concentrate based GSH (PWP-GSH) was prepared according to Example 1 with polymerized whey protein concentration of 10% and whey protein and GSH ratio of 1:1. The prepared polymerized whey protein GSH was then dried using a freeze drier (Alpha 1-4 LDplus, Germany). Then the powdered polymerized whey protein based GSH was incorporated into normal feeds at the percentage of 0.5%, 1% and 4% (w/w) which corresponds to 0.25%, 1% and 2% percentage for GSH. The diets were prepared by Beijing HFK Bioscience Co., Ltd (Beijing, China). The dose was set based on the daily intake for health human (100 mg per day). The dose for human will be 1.6 mg/kg calculated with average weight of 60 Kg. According to the conversion equation, it equals to 10 mg/kg for rats. The does was set to be 0.5%, 1% and 4% which are corresponding to 25, 50 and 200 folds of human daily intake.

Experimental Design

Eighty rats (male and female for half) at age of 3 weeks were purchased from Beijing HFK Bioscience Co., Ltd (Beijing, China). All rats were housed in plastic lab animal cages in a ventilated room. The room was maintained at 20±2° C. and 60±10% relative humidity with a 12 h light/dark cycle. Water was available ad libitum. Subject rats were acclimated to this environment for 7 days before treatment in which there were no apparent changes in general status. Following acclimatization, rats were randomly allocated to four groups (10 per sex per group) based on body weight means. Individual body weight of a group at randomization was within ±20% of the overall mean. Compared to the animals in control groups, the low, mid and high-dose group animals received 0.5%, 1% and 4% whey protein based GSH in their diets, respectively. All animal experiments were approved by the Animal Welfare and Research Ethics Committee at Jilin University (Approval ID: SY201905018).

Clinical Observations

Coat condition, skin, mucous membranes, occurrence of secretions and excretions, autonomic nervous system activity, changes in gait, and posture of each rat were observed throughout the study.

Body Weight and Food Intake

Individual body weights as well as body weights at the interval of 4 days were weighed and recorded for a total period of 28 days. Final body weights (fasted) were recorded prior to the scheduled necropsy. Feed intake was also measured and expressed as the mean food consumption (expressed as g/rat/day) was calculated for the corresponding intervals.

Blood Collection

At the termination of the experiment, all animals were fasted for 12 h prior to blood collection but did have access to water. Rats were injected for 2% pentobarbital sodium solution at the level of 0.2 ml/100 g. Then, two separate blood samples for hematology and serum chemistry were collected via heart. For hematology analysis, the blood samples were collected by EDTA-2K coated tubes and then determined for white blood cells (WBC), red blood cells (RBC), hemoglobin (HGB), hematocrit (HCT), blood platelet count (PLT), mean corpuscular volume (MCV), mean corpuscular hemoglobin (MCH), mean corpuscular hemoglobin concentration (MCHC), red cell volume distribution (RDW), mean platelet volume (MPV) lymphocyte (LYM), neutrophilicgranulocyte (GRAN), monocyte (MONO), Lymphocyte (LYM %), granulocyte (GRA), Percent monocytes (MON %) using Exigo animal hematology analyzer.

For serum chemistry analysis, the blood sample was centrifuged at 10000 rpm at room temperature for 3 min. The upper serum was transferred to a new centrifugal tube and then determined for albumin (ALB), calcium (Ca), creatinine (Crea), total bilirubin (TB), TotalProtein (TP), inorganic phosphorus (PHOS), urea (UREA), amylase (AMY), triglyceride (TG), glucose (GLU), the ratio of BUN to CR (U/C), creatine kinase (CK), Globulin (GLOB), aspartate aminotransferase (AST) using Smt-120v automatic biochemical analyzer.

Organ Weights, Gross Necropsy and Histopathology

At termination, all the rats were anaesthetized by pentobarbital sodium and exsanguinated by transecting the anocelia. Then a complete gross pathology examination was conducted by visual inspection during necropsy. Brain, heart, lung, liver, spleen, kidney, bladder, ovary, uterus, testes, epididymis and seminal vesicles for all animals were excised and weighed. Relative weight of each organ (or paired organs) was calculated based on final individual body weight measured on the day of termination. Tissue sections from these organs were fixed with 10% buffered formaldehyde except testes were fixed in Bouin solution, embedded in paraffin, sectioned at 2-5 μm, mounted on glass microscope slides, stained with standard hematoxylin-eosin and examined using light microscopy. All the histopathology procedures were carried out in College of Animal Science and Veterinary Medicine, Jilin University.

Results

During the course of the experiment, there was no observed adverse effects in the experimental group compared with the control group.

Figure 7:
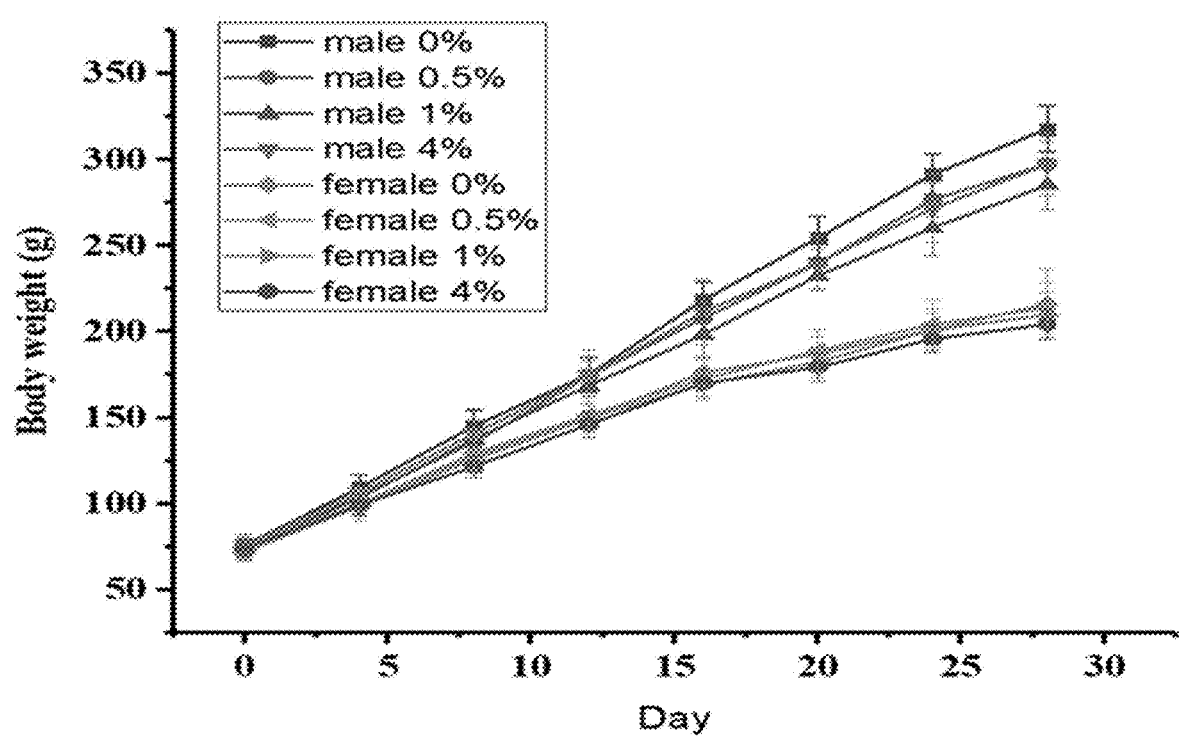
FIG. 7 depicts, in another embodiment, body weight curves in rats in grams in 28-day feeding test incorporating PWP-GSH in feed.

During the course of the experiment, no treatment-related signs of adverse effects in clinical appearance of the animals were observed. Body weight increased gradually as the treatment period progressed (FIG. 7). There was no statistically significant difference in body weight between female groups. For male groups, from 16 days, 1% male groups were significantly different from those of control. The body weight changes were observed only in male group and there was no dose-dependent effect.

Figure 8:
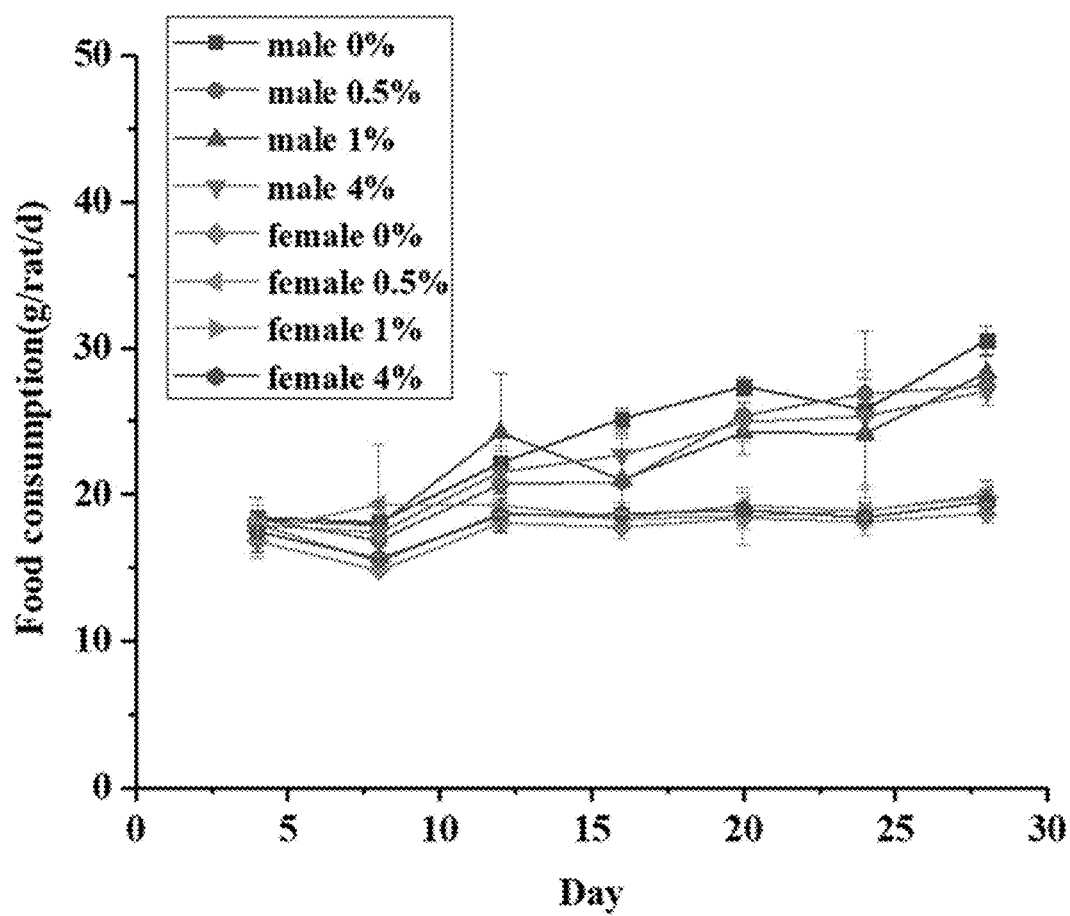
FIG. 8 depicts, in another embodiment, food consumption curves in rats in grams/rat/day in 28-day feeding test incorporating PWP-GSH in feed.
Figure 9:
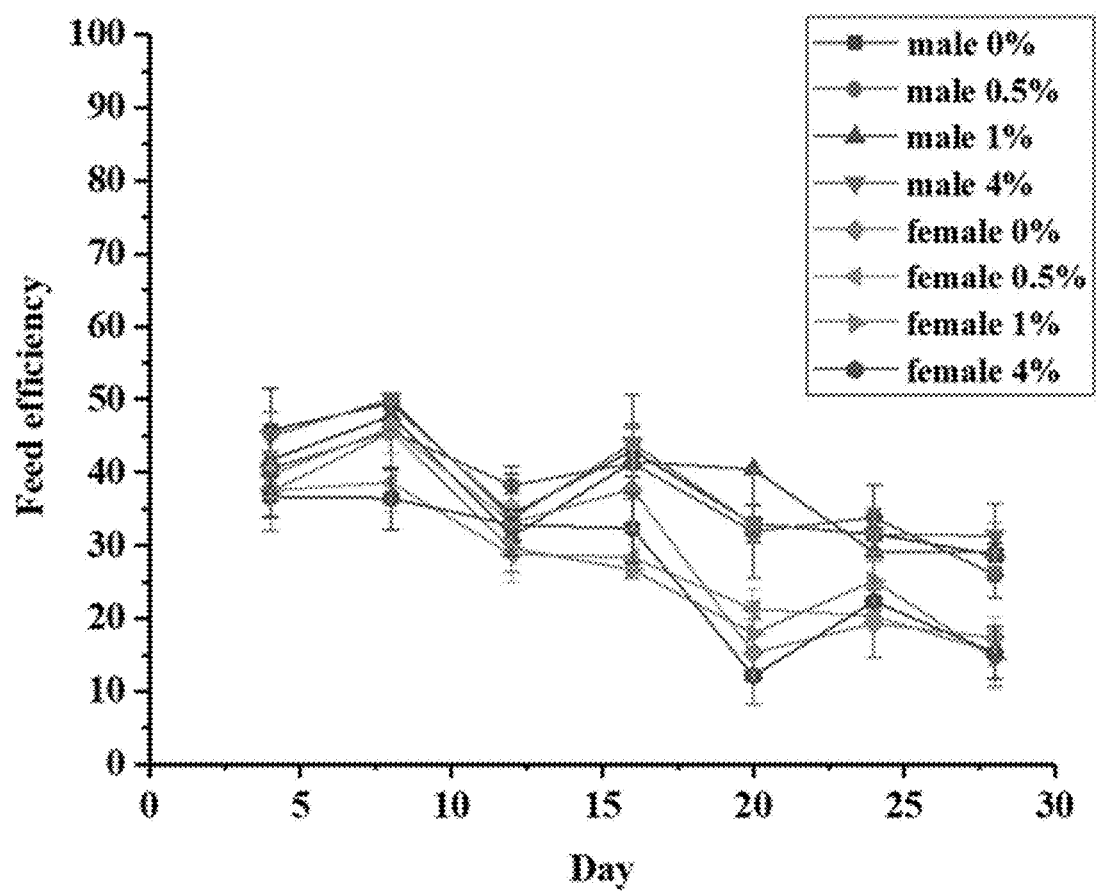
FIG. 9 depicts, in another embodiment, food efficiency curves in rats in 28-day feeding test incorporating PWP-GSH in feed.

Results for food consumption and food efficiency of rats for 28 days are shown in FIGS. 8 and 9. There was no PWPC-GSH related toxicity effect observed in experimental groups although there was some significant difference between experimental group and control at some time point. Groups of 0.5% and 4% female showed significant difference in food efficiency compared with control at $8^{th}$ day ($p<0.05$).

Table 3 shows serum biochemistry for male rats in the 28-day toxicity study.

Results for the serum biochemistry of male rats are shown above in Table 3. Albumin in the 4% male group shows value of 33.01±1.34 g/L, which was significantly lower than that of control group ($p<0.05$). The low content of albumin in serum maybe due to synthesis deficiency. Two reasons may be responsible for this change. Due to hepatitis, albumin absorption by liver may be decreased. The other reason may be the renal excretion dysfunction caused by low nephrogenic which may cause the excretion of a large amount of albumin along with urine. Globulin in 4% male is 28.1±2.77 g/L, which was significantly lower than that of control group ($p<0.05$). However, the value is in the normal range (15-28 g/L). Aspartate aminotransferase in 4% male was 91.17±8.13 U/L, which was significantly lower than that of control group ($p<0.05$). However, the value was also in the normal range (39-111 U/L). Alanine aminotransferase in 4% male was 39±7.73 U/L, which was significantly lower than that of control ($p<0.05$). However, the value was in the normal range (20-61 U/L). Aspartate aminotransferase and alanine aminotransferase are the indicators for liver function. Increase in the two parameters may indicate some pathological change in liver and decrease may be not clinically significant. Compared with control, all experimental groups showed significantly lower amylase values ($p<0.05$), which was a benefit. Creatine kinase values in experimental groups were significantly lower than that of control groups ($p<0.05$), which was a benefit. Glucose in 4% male was significantly lower than that of control group and was in the normal range (2.78-7.50 μmon). Calcium level in 1% and 4% male groups were significantly lower than that in control group ($p<0.05$). Decrease in calcium level may be due to (1) deficiency in parathyroid hormone; (2) Vitamin D deficiency or metabolic abnormality; (3) chronic kidney disease.

In conclusion, significant changes in serum biochemistry were mainly observed in the 4% male group and are mostly related with function of liver or kidney.

Table 4 shows serum biochemistry for female rats in the 28-day toxicity study (n=10).

TABLE 3

|  | 0% | 0.5% | 1% | 4% |
|---|---|---|---|---|
| Albumin (g/L) | 34.78 ± 1.05 | 33.90 ± 1.34 | 33.53 ± 0.99 | 33.01 ± 1.34* |
| Total protein (g/L) | 66.39 ± 4.69 | 63.52 ± 3.90 | 62.75 ± 2.46 | 59.11 ± 7.98 |
| Globulin (g/L) | 32.71 ± 3.08 | 29.62 ± 3.13 | 29.22 ± 2.36 | 28.1 ± 2.77* |
| Globulin ratio | 1.12 ± 0.14 | 1.15 ± 0.11 | 1.16 ± 0.10 | 1.18 ± 0.10 |
| Total bilirubin (μmol/L) | <1.0 | <1.0 | <1.0 | <1.0 |
| Aspartate aminotransferase (U/L) | 138.20 ± 17.63 | 105.00 ± 11.51* | 81.60 ± 10.14* | 91.17 ± 8.13* |
| Alanine aminotransferase (U/L) | 45.70 ± 5.85 | 43.89 ± 6.31 | 40.50 ± 4.55 | 39 ± 7.73* |
| Amylase (U/L) | 2320.37 ± 178.97 | 1898.71 ± 145.35* | 2009.2 ± 194.24* | 1775.0 ± 110.55* |
| Creatinine (μmol/L) | <4 | <4 | <4 | <4 |
| Creatine kinase (U/L) | 1110.00 ± 92.28 | 723.00 ± 64.50* | 354.00 ± 32.04** | 413.40 ± 31.05** |
| Triglyceride (μmol/L) | 0.77 ± 0.37 | 0.51 ± 0.26 | 0.56 ± 0.17 | <0.3 |
| Glucose (μmol/L) | 7.92 ± 0.95 | 7.17 ± 0.51 | 7.03 ± 1.12 | 6.203 ± 0.51833* |
| Calcium (μmol/L) | 2.57 ± 0.05 | 2.50 ± 0.08 | 2.45 ± 0.0 ** | 2.379 ± 0.10** |
| Inorganic phosphorus (μmol/L) | 3.35 ± 0.31 | 3.03 ± 0.36 | 3.25 ± 0.48 | 2.70 ± 0.23 |
| BUN (μmol/L) | 5.06 ± 0.58 | 4.52 ± 0.69 | 5.13 ± 0.72 | 4.48 ± 0.88 |

Note:
*means significant level of 0.05,
**means significant level of 0.01 compared with the control group

TABLE 4

|  | 0% | 0.5% | 1% | 4% |
| --- | --- | --- | --- | --- |
| Albumin (g/L) | 34.91 ± 1.28 | 34.53 ± 1.35 | 36.14 ± 1.56 | 34.04 ± 1.11 |
| Total protein (g/L) | 64.32 ± 2.90 | 63.82 ± 3.95 | 68.02 ± 4.31* | 64.47 ± 3.50 |
| Globulin (g/L) | 29.42 ± 2.22 | 29.29 ± 3.29 | 31.88 ± 3.47 | 30.42 ± 2.75 |
| Globulin ratio | 1.19 ± 0.09 | 1.19 ± 0.12 | 1.15 ± 0.13 | 1.13 ± 0.09 |
| Total bilirubin (μmol/L) | <1.0 | <1.0 | <1.0 | <1.0 |
| Aspartate Aminotransferase (U/L) | 87.20 ± 10.32 | 103.16 ± 8.70 | 99.50 ± 9.98 | 134.50 ± 5.44 |
| Alanine Aminotransferase (U/L) | 40.00 ± 4.50 | 41.62 ± 3.54 | 38.25 ± 3.86 | 40.28 ± 3.35 |
| Amylase (U/L) | 1442.25 ± 148.93 | 1464.66 ± 147.65 | 1220.55 ± 125.14* | 1191.37 ± 120.09* |
| Creatinine (μmol/L) | <4 | <4 | <4 | <4 |
| Creatine kinase (U/L) | 1054.60 ± 197.79 | 411.20 ± 43.84 | 540.50 ± 90.78 | 363.00 ± 61.57 |
| Triglyceride (μmol/L) | 0.42 ± 0.21 | 0.43 ± 0.27 | 0.38 ± 0.17 | 0.35 ± 0.09 |
| Glucose (μmol/L) | 8.66 ± 0.82 | 8.16 ± 1.48 | 6.89 ± 0.58** | 6.40 ± 1.02** |
| Calcium (μmol/L) | 2.49 ± 0.09 | 2.53 ± 0.07 | 2.55 ± 0.08 | 2.51 ± 0.11 |
| Inorganic phosphorus (μmol/L) | 2.48 ± 0.31 | 2.98 ± 0.37* | 2.89 ± 0.23* | 3.02 ± 0.42* |
| BUN (μmol/L) | 5.07 ± 0.97 | 4.91 ± 1.19 | 5.68 ± 0.52 | 5.61 ± 1.74 |

Note:
*means significant level is 0.05,
**means significant level is 0.01 compared with the control group Results for serum biochemistry of female rats are shown in Table 4. Total protein in 1% female group was 68.02±4.31 g/L, which was significantly higher than that of the control group ($p<0.05$). However, it was in the normal range (53-69 g/L). Increased total protein level may be due to chronic liver disease. Amylase and glucose in 1% and 4% females were significantly lower than that of control group ($p<0.05$). Inorganic phosphorus level in 1% and 4% female groups were significantly higher than control group. However, they were in the normal range (1.87-3.6 μmon).

Hematology

Table 5 shows hematology for male rats in the 28-day toxicity study (number of animals=10).

TABLE 5

|  | 0% | 0.5% | 1% | 4% |
| --- | --- | --- | --- | --- |
| RBC ($10^{12}$/L) | 6.26 ± 1.07 | 6.589 ± 0.46 | 6.63 ± 0.20 | 6.50 ± 0.42 |
| MCV (fL) | 63.74 ± 2.64 | 62.85 ± 2.45 | 61.72 ± 1.91 | 61.73 ± 1.21 |
| RDW % | 21.64 ± 0.22 | 21.72 ± 0.37 | 21.73 ± 0.42 | 21.57 ± 0.22 |
| RDWa (fL) | 39.80 ± 2.18 | 39.08 ± 1.96 | 38.58 ± 1.82 | 40.11 ± 2.19 |
| HCT % | 39.82 ± 2.72 | 41.42 ± 3.36 | 40.93 ± 1.11 | 40.11 ± 2.20 |
| PLT ($10^9$/L) | 900.50 ± 27.50 | 1280.50 ± 97.06 | 1192.20 ± 104.45 | 1162.16 ± 98.46* |
| MPV (fL) | 6.96 ± 0.27 | 6.38 ± 0.40* | 6.55 ± 0.29 | 6.39 ± 0.18* |
| WBC ($10^9$/l) | 4.20 ± 2.19 | 4.60 ± 1.12 | 3.42 ± 1.07 | 3.88 ± 1.50 |
| HGB (g/dL) | 13.78 ± 2.14 | 14.13 ± 1.30 | 14.22 ± 0.37 | 14.09 ± 0.77 |
| MCH (pg) | 22.10 ± 1.11 | 21.48 ± 1.11 | 21.43 ± 0.67 | 21.71 ± 0.47 |
| MCHC (g/dL) | 0.78 ± 0.35 | 0.65 ± 0.27 | 0.21 ± 0.09 | 0.29 ± 0.09 |
| LYM (g/dL) | 3.44 ± 1.76 | 4.05 ± 1.06 | 2.98 ± 0.93 | 3.39 ± 1.32 |
| GRAN (g/dL) | 0.62 ± 0.43 | 0.43 ± 0.30 | 0.33 ± 0.15 | 0.38 ± 0.23 |
| MONO (g/dL) | 0.14 ± 0.05 | 0.12 ± 0.041 | 0.1 ± 0 | 0.11 ± 0.03 |
| LYM % | 83.24 ± 4.25 | 90.76 ± 1.96* | 87.23 ± 1.48 | 87.62 ± 3.62 |
| GRA % | 83.24 ± 4.25 | 88.30 ± 6.28 | 87.23 ± 1.49 | 87.62 ± 3.62 |
| MON % | 1.98 ± 0.24 | 1.47 ± 0.58 | 1.70 ± 0.45 | 1.57 ± 0.41 |

Note:
*means significant level is 0.05,
** means significant level is 0.01 compared with the control group There were no treatment-related adverse effects of PWPC-GSH powder on hematology parameters in male rats. However, some statistically significant differences occurred between control and treatment groups. PLT, MPV in 4% groups were significantly different from those of the control ($p<0.05$). MPV and LYM in 0.5% group were also significantly different from those of the control ($p<0.05$).

Table 6 shows hematology for female rats in the 28-day toxicity study (number of animals=10).

TABLE 6

|  | 0% | 0.5% | 1% | 4% |
|---|---|---|---|---|
| RBC ($10^{12}$/L) | 6.25 ± 0.30 | 6.53 ± 0.35 | 6.76 ± 0.56* | 6.61 ± 0.28 |
| MCV (fL) | 58.75 ± 2.07 | 59.71 ± 1.45 | 59.74 ± 2.29 | 59.26 ± 1.70 |
| RDW % | 20.95 ± 0.45 | 20.90 ± 0.38 | 20.86 ± 0.23 | 21.10 ± 0.39 |
| RDWa (fL) | 35.08 ± 1.46 | 35.87 ± 1.14 | 35.89 ± 1.87 | 35.88 ± 1.40 |
| HCT % | 36.73 ± 1.78 | 38.96 ± 1.60 | 40.30 ± 2.64 | 39.11 ± 1.29 |
| PLT ($10^9$/L) | 1098.00 ± 122.18 | 1271.00 ± 130.77 | 1330.57 ± 122.96 | 1286.00 ± 165.89 |
| MPV (fL) | 6.75 ± 0.73 | 6.30 ± 0.35 | 6.45 ± 0.38 | 6.46 ± 0.48 |
| WBC ($10^9$/L) | 3.81 ± 2.17 | 4.64 ± 1.34 | 5.86 ± 1.76 | 4.01 ± 0.93 |
| HGB (g/dL) | 13.18 ± 0.56 | 13.97 ± 0.55 | 14.46 ± 0.88* | 14.10 ± 0.36* |
| MCH (pg) | 21.13 ± 0.61 | 21.41 ± 0.48 | 21.48 ± 0.73 | 21.40 ± 0.63 |
| MCHC (g/dL) | 35.99 ± 0.43 | 35.87 ± 0.38 | 35.95 ± 0.47 | 36.10 ± 0.35 |
| LYM (g/dL) | 3.19 ± 1.65 | 3.94 ± 1.13 | 5 ± 1.26 | 3.43 ± 0.59 |
| GRAN (g/dL) | 0.51 ± 0.54 | 0.57 ± 0.25 | 0.70 ± 0.53 | 0.48 ± 0.38 |
| MONO (g/dL) | 0.13 ± 0.05 | 0.14 ± 0.07 | 0.16 ± 0.07 | 0.13 ± 0.051 |
| LYM % | 84.91 ± 5.25 | 84.80 ± 5.03 | 86.20 ± 4.43 | 85.94 ± 5.29 |
| GRA % | 84.91 ± 5.25 | 84.80 ± 5.03 | 86.20 ± 4.43 | 85.94 ± 5.29 |
| MON % | 84.91 ± 5.25 | 84.80 ± 5.03 | 86.20 ± 4.43 | 85.94 ± 5.29 |

Note:
*means significant level is 0.05,
** means significant level is 0.01 compared with the control group There were no treatment-related adverse effects of PWPC-GSH powder on hematology parameters in female rats. However, some statistically significant differences occurred between control and treatment groups. Compared with control, RBC in the 1% group showed significantly higher value of 6.76±0.56×1012/L (p<0.05). This change may be caused by lack of water and should not be considered as test-substance related. HGB in the 1% female group (14.46±0.88 g/dL) and the 4% female group (14.10±0.36 g/dL) were significantly higher than control (p<0.05). However, the values were in the normal range (13.2-16.4 g/dL) and should not be considered as adverse effects.

Relative Organ Weights

Results for relative organ weights are shown in Tables 7 and 8. Male rats with PWPC-GSH powder showed significantly lower final body weight then the control group (p<0.05). Compared with control, there was no significant difference in relative organ weights for organs for all rats fed with PWPC-GSH powder except for liver and kidney in the 4% male group.

Table 7 shows relative organ weights for male rats in the 28-day toxicity study (number of animals=10).

TABLE 7

|  | 0% | 0.5% | 1% | 4% |
|---|---|---|---|---|
| Body weight | 296.8 ± 11.47 | 272.78 ± 10.28** | 261 ± 12.59** | 275 ± 18.70* |
| Brain | 5.35 ± 0.85 | 5.90 ± 2.11 | 6.45 ± 0.63* | 6.67 ± 0.67 |
| Thymus | 2.58 ± 0.60 | 3.01 ± 0.42 | 2.37 ± 0.38 | 2.66 ± 0.47 |
| Heart | 3.80 ± 0.30 | 4.03 ± 0.50 | 3.92 ± 0.28 | 3.89 ± 0.28 |
| Lung | 4.74 ± 0.38 | 5.31 ± 1.08 | 4.98 ± 0.52 | 4.78 ± 0.31 |
| Liver | 39.00 ± 4.33 | 37.22 ± 4.83 | 36.62 ± 2.96 | 34.92 ± 2.83* |
| Spleen | 2.79 ± 0.92 | 2.78 ± 0.72 | 2.47 ± 0.35 | 2.79 ± 0.39 |
| Kidney | 9.16 ± 0.70 | 9.32 ± 0.39 | 9.38 ± 0.38 | 9.66 ± 0.51* |
| Bladder | 0.28 ± 0.04 | 0.31 ± 0.07 | 0.32 ± 0.05 | 0.29 ± 0.07 |
| Testes | 6.796 ± 1.79 | 8.62 ± 1.05 | 8.25 ± 0.23 | 8.67 ± 0.76 |
| Epididymis | 0.57 ± 0.11 | 0.48 ± 0.15 | 0.58 ± 0.09 | 0.59 ± 0.05 |
| Seminal Vesicle | 1.95 ± 0.58 | 1.47 ± 0.42 | 1.11 ± 0.68 | 1.59 ± 0.50 |

Note:
*means significant level is 0.05,
**means significant level is 0.01 compared with the control group For female rat, rats in the 4% group showed significantly lower final body weight (p<0.05). There was no significant difference in relative organ weights between rats fed with PWPC-GSH powder and control group.

Table 8 shows relative organ weights for female rats in the 28-day toxicity study (number of animals=10).

TABLE 8

|  | 0% | 0.5% | 1% | 4% |
|---|---|---|---|---|
| Body weight | 203.80 ± 10.14 | 205.20 ± 16.01 | 199.70 ± 11.93 | 192.10 ± 8.77* |
| Brain | 7.14 ± 1.40 | 8.52 ± 0.86 | 8.22 ± 1.02 | 8.65 ± 0.84 |
| Thymus | 3.36 ± 0.46 | 3.31 ± 0.38 | 3.40 ± 0.52 | 3.31 ± 0.44 |
| Heart | 6.82 ± 0.86 | 3.99 ± 0.26 | 4.26 ± 0.37 | 4.08 ± 0.31 |

TABLE 8-continued

|  | 0% | 0.5% | 1% | 4% |
|---|---|---|---|---|
| Lung | 5.44 ± 0.55 | 5.09 ± 0.39 | 5.19 ± 0.35 | 5.13 ± 0.33 |
| Liver | 35.76 ± 2.74 | 38.28 ± 7.27 | 34.54 ± 2.14 | 36.08 ± 1.55 |
| Spleen | 2.51 ± 0.32 | 2.56 ± 0.40 | 2.32 ± 0.34 | 2.57 ± 0.21 |
| Kidney | 8.83 ± 0.46 | 8.54 ± 1.53 | 8.70 ± 0.31 | 9.47 ± 0.51 |
| Bladder | 0.35 ± 0.03 | 0.36 ± 0.07 | 0.35 ± 0.04 | 0.35 ± 0.06 |
| Ovary | 0.71 ± 023 | 1.65 ± 0.28 | 0.54 ± 0.16 | 0.56 ± 0.14 |
| Uterus | 2.11 ± 0.62 | 1.98 ± 0.62 | 1.75 ± 0.65 | 1.99 ± 0.98 |

Figure 10A:
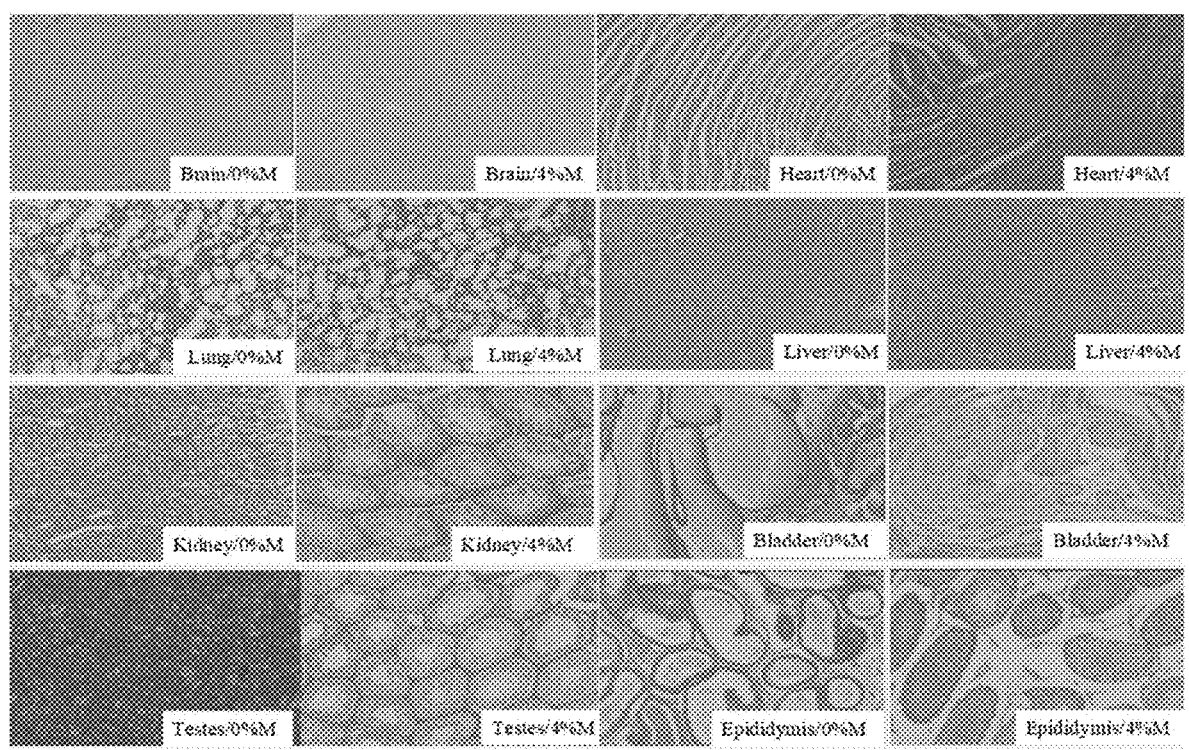
FIG. 10A depicts, in an embodiment, microscope images of stained sections of several organ tissues in male rats in 28-day feeding test incorporating 4% by wt. PWP-GSH in feed vs. control.
Figure 10B:
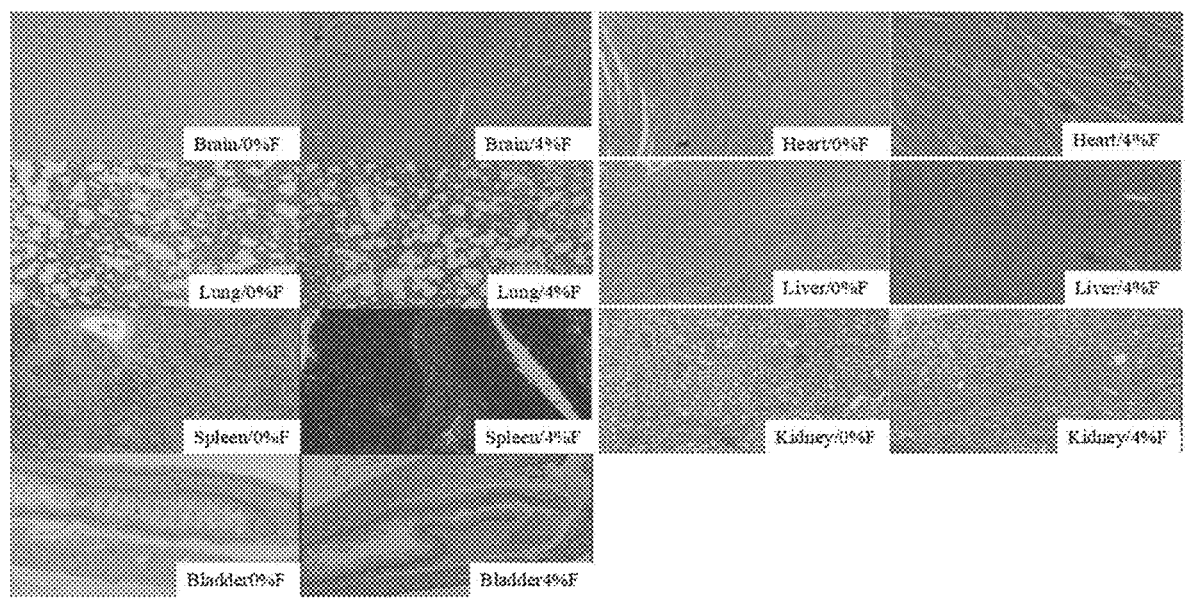
FIG. 10B depicts, in an embodiment, microscope images of stained sections of several organ tissues in female rats in 28-day feeding test incorporating 4% by wt. PWP-GSH in feed vs. control.

Note:
*means significant level is 0.05,
** means significant level is 0.01 compared with the control group Pathology and Histopathology FIGS. 10A and 10B show stained sections of several tissues in male and female rats in the 4% feeding group vs. control. Tissue samples were prepared and stained by the usual method, and viewed by standard microscopic methods.

Conclusions

The results of PK studies indicated that the serum uptake of polymerized whey protein encapsulated GSH (PWP-GSH) was three times higher than that of Kyowa's Setria GSH. The levels of GSH in brain and liver tissues for the rats fed with polymerized whey protein encapsulated GSH compared with the group fed with commercial GSH diet were significant higher after 3-4 hours of administration. Compared with control, there are some changes in parameters of body weight, serum biochemistry and relative organ weights in the 4% feeding male group. Thus, it can be concluded that the no-observed-adverse-effects level (NOAEL) was estimated to be at least 1% for male rats and 4% for female rats which are corresponding to about 50 and 200 folds of human daily intake value.

In summary, the bioavailability of whey protein encapsulated GSH (WP-GSH, PWP-GSH) was much improved compared with the standard control and it is a safe form of delivery system.

Example 3

Preparation of Polymerized Whey Protein Encapsulated Glutathione (PWP-GSH)

Whey protein concentrate (5 Kg) was dissolved in distill water at the concentration of 10% (w/v) and stored at 4° C. overnight. The whey protein concentrate solution was then heated at 80° C. for 15 minutes. After cooling to room temperature, the PWPC solution was then mixed with GSH powder (5 Kg) at weight ratios of PWPC:GSH=1:1. The mixtures were stirred for 20 min for the complete dissolution. After blending, the mixture was then freeze-dried to provide a PWP-GSH powder product.

Reduced glutathione (GSH) assay kit (A006-2-1), total antioxidative capacity measurement kit (ABTS method) (A015-2-1) is available from Nanjing Jiancheng Bioengineering Institute (Nanjing, Jiangsu China). GSH content may be assayed using several methods. The following procedure provided a determination of GSH content without digestion.

PWPC based GSH powder (2 g) was dissolved in 20 mL PBS buffer and then sonicated for 20 min for the complete extraction. After sonication, 1 mL supernatant was taken and diluted for 800 folds. Then, 1 mL diluted solution was mixed with 1 mL protein removing agent and then centrifuged at 3500 rpm for 10 min. The supernatant was then determined for GSH content using GSH assay kit.

Alternatively, GSH content was determined after trypsin digestion.

Releasing solution: trypsin (10 g) with enzyme activity of 1:250 was dissolved in 1 L NaCl solution (0.5%, w/v) and then adjusted to pH 8 using 0.1 M NaOH solution. PWPC based GSH powder (0.3 g) placed into 30 mL releasing solution and incubated while shaking at 100 rpm at 37° C. for 6 h. The mixture was then centrifuged at 5,000×g for 20 min and then the supernatant was diluted for 100 folds. The diluted suspension was then mixed with protein removing solution at ratio of 1:1 (v/v) and then centrifuged. The supernatant was then determined for GSH content using GSH assay kit.

Figure 11:
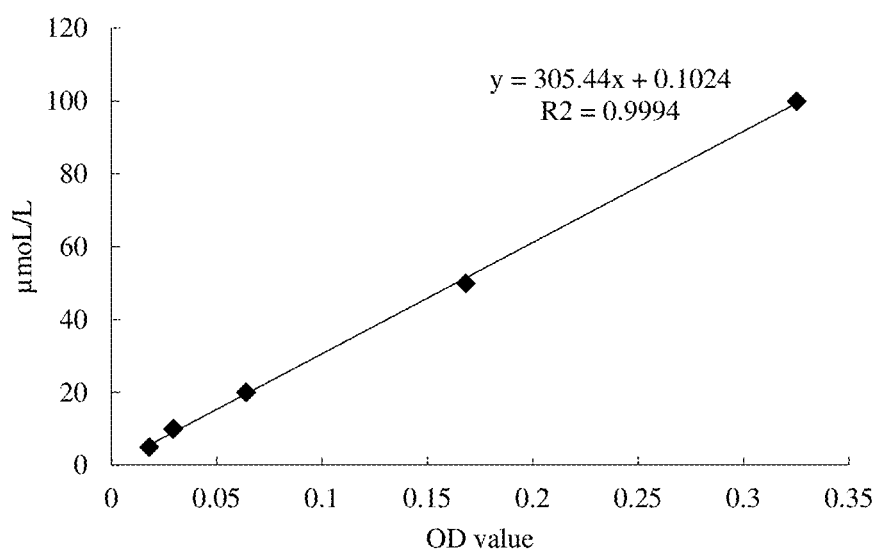
FIG. 11 depicts a standard curve for determining reduced GSH content in a solid sample using a reduced glutathione (GSH) assay kit (A006-2-1).

Referring to FIG. 11 standard curve, without digestion, the OD values of two samples were 0.2883 and 0.2862, respectively, which correspond to the content of 43.2% and 42.9% (w/w) of GSH in the PWPC-GSH product. After trypsin digestion, the OD values of the two samples were 0.2654 and 0.2627, respectively, which correspond to 49.8% and 49.2% (w/w) of GSH in the PWPC-GSH product.

Therefore, the processing technology for whey protein encapsulated GSH (PWP-GSH) manufacturing has been established and the recovery rate of glutathione in the matrix was 99.2%, indicating that the loss of this heat sensitive compound was only 0.8% throughout the process.

Example 4

Chemical characterization of PWP-GSH samples. It is well understood that samples made in accordance with the principles of this disclosure may be characterized by various means well known in the art, including, but not limited to, viscosity measurements and other rheological measurements, FT-IR, TEM/SEM photomicrography, microstructure and morphology studies, stability studies (solid phase, solution phase, humidity, thermal), particle size, Zeta potential, and the like. It is expected that the said chemical analyses will further show the unique qualities and properties of the compositions described herein. Cf. Khan, et al., 2019.

Example 4A

1. Preparation of PWPC-GSH Using Whey Protein Concentrate (PWC)

PWPC-GSH system was prepared with advantages of simplicity, mildness, and organic solvent-free in comparison with other carriers based on poly isobutylcyanoacrylate, Eudragit RS 100/cyclodextrin and montmorillonite. In one characterization test measured in accordance with Zhang et al. (2021), PWPC exhibited bimodal pattern with two peaks at 594 nm and 4580 nm with a wide particle size distribution (span of 9.22), consistent with previous research. Combination with GSH (287.83±6.18 nm) slightly increased particle size (D50) from 1085±35.35 to 1115±7.07 nm with decreased span from 9.22±0.22 to 6.86±0.19. Zeta potential for PWPC-GSH was found to be 30.37±0.75 mV. The high surface charge endowed the PWPC-GSH system high stability since strong electrostatic repulsion between molecules prevents polymerization, precipitation, and flocculation. In addition, the positive surface charge of PWPC-GSH would favor absorption in vivo since cell membranes carries negative charges. PWPC-GSH system displayed shear-thinning behavior in range of 1-300 s-1, indicating that interaction between droplets was weakened at higher shear rate.

Figure 12:
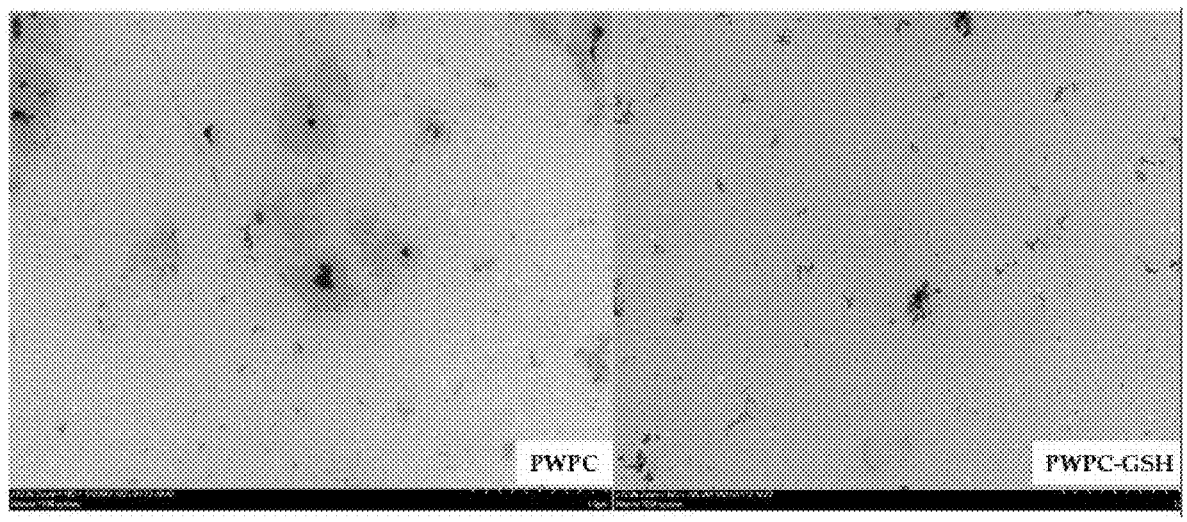
FIG. 12 depicts TEM images of PWPC and PWPC-GSH determined using standard techniques. Gradations at bottom are 1.0 micrometer.

A DSC thermogram of GSH demonstrated an exothermic peak at 198° C. and disappearance of this melting peak in the PWPC-GSH system, implying that GSH was molecularly dispersed in PWPC particles. FTIR spectra analysis showed that PWPC displayed an amide I (C=O vibration) spectrum peak at 1654.39 cm-1 and red shift occurred after binding with GSH, indicating that PWPC was structurally changed and intermolecular hydrogen bonds formed. This PWPC-GSH system exhibited morphology of vermicular aggregates with its majority at a size of roughly 200 nm, with some larger aggregates measuring upwards of approximately 400 nm, determined by standard TEM imaging techniques (FIG. 12).

2. In Vivo Pharmacokinetic and Antioxidant Activity of PWPC-GSH

Whey protein has been widely studied as an effective means of nutrient delivery due to its resistance to digestion by pepsin, its non-toxic nature, widely available sources and broad biocompatibility. Pharmacokinetic studies of the PWPC-GSH delivery system and free GSH were conducted and plasma GSH concentration-time profiles for all groups were determined. GSH concentration was observed to be the highest in the plasma of PWPC-GSH group, followed by free GSH, PWPC, and the control group. The higher value in the plasma of mice gavage with PWPC-GSH than that of free GSH group may be due to the protection effect of highly viscous PWPC by embedding GSH inside and preventing damage to gastrointestinal enzymes and an acidic environment. These results were consistent with previous studies that the bioavailability of quercetin and vitamin D were improved through whey protein encapsulating.

Pharmacokinetic parameters were calculated using a mouse model. Compared with free GSH (maximum concentration ($C_{max}$) of 7.37 mg/L and area under the concentration-time curve (AUC) of 19.23 h×mg/L, higher $C_{max}$ (19.41 mg/L) and AUC (48.63 h×mg/L) values were observed, indicating a higher rate and degree of GSH absorption in the blood circulation in mice after administration with PWP-GSH. The 2.5-fold and 2.6-fold higher $C_{max}$ and AUC in the PWPC-GSH group suggested that the PWPC-GSH delivery system can improve the in vivo bioavailability of GSH effectively vs. GSH in its pure form on its own. Whey protein also appears to possess a protective effect on GSH as a carrier during absorption into the intestinal tract which may be due to the resistance to digestion by pepsin. In addition to delivery of the GSH itself, the whey protein supplementation may have also contributed to the increase in GSH levels in vivo by virtue of the abundance of cysteine residue inherent to whey protein, which has the capability to pro-mote biosynthesis of GSH as a rate-limiting amino acid. The lower time to maximum concentration (Tmax) (1 h) occurred in the PWPC-GSH group in comparison with that in free GSH (2 h), indicating less time was required to reach the maximum concentration after administration. The plasma concentration of GSH in the GSH group reached its maximum levels after 1.5 to 2 h which echoed data reported in the early literature relative to orally administered free GSH.

Total antioxidative capacity of samples at different time points was measured using an assay kit. Antioxidant capacity of plasma in mice gavage with PWPC-GSH was significantly higher than that of free GSH through the whole period (p<0.05). The first reason for the increased antioxidant capacity of plasma after gavage of PWPC-GSH in mice was that GSH concentration in plasma was improved using PWPC as a delivery carrier. The second reason may be due to the antioxidant properties of whey protein. As measured by T-AOC (mM), the plasma antioxidant capacity of mice after gavage with PWPC was also slightly improved to a degree that may or may not be consistent with an additive effect.

Example 4B

In accordance with Examples 3, 4 and 4A, various parameters were measured for PWPC-GSH and PWPI-GSC, compared with whey protein concentrate (WPC) and whey protein isolate (WPI) standards.

Figure 13A:
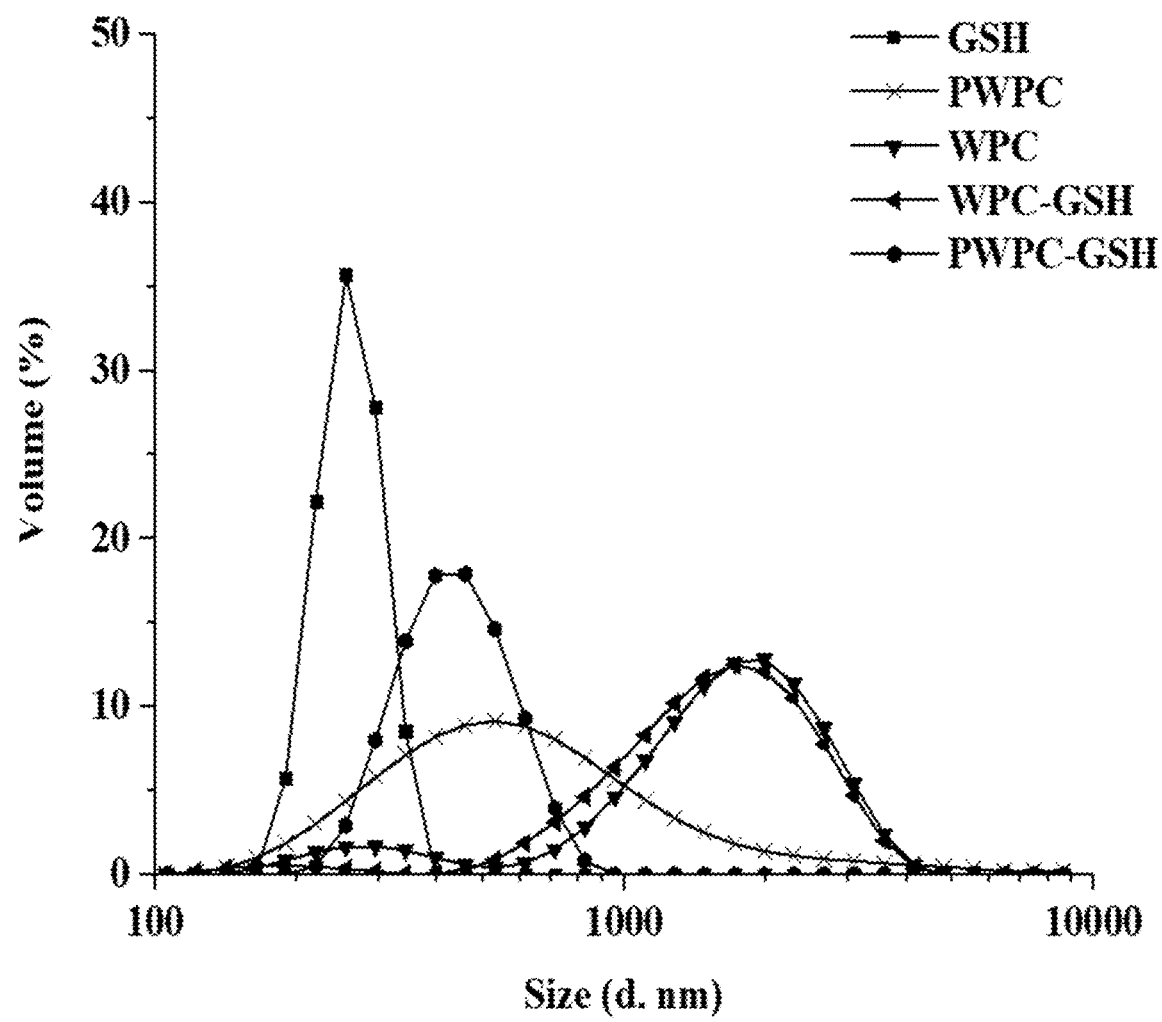
FIG. 13A depicts particle size distribution of whey protein encapsulated glutathione nanoparticles, for example, PWPC-GSH, based on WPC.
Figure 13B:
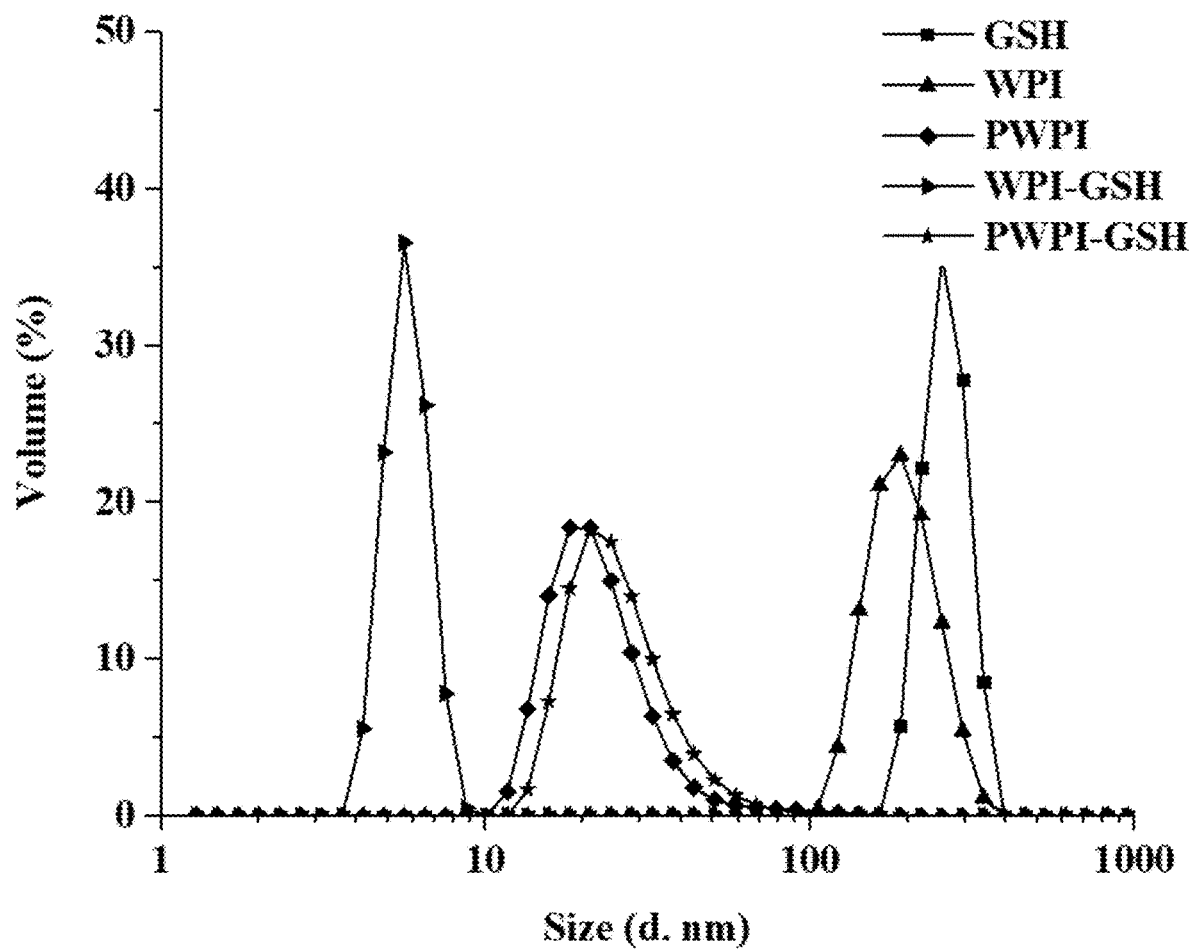
FIG. 13B depicts particle size distribution of whey protein encapsulated glutathione nanoparticles, for example, PWPI-GSH, based on WPI.

FIGS. 13A and 13B show particle size distribution of whey protein encapsulated glutathione nanoparticles for WPC and WPI starting materials, respectively.

Figure 14:
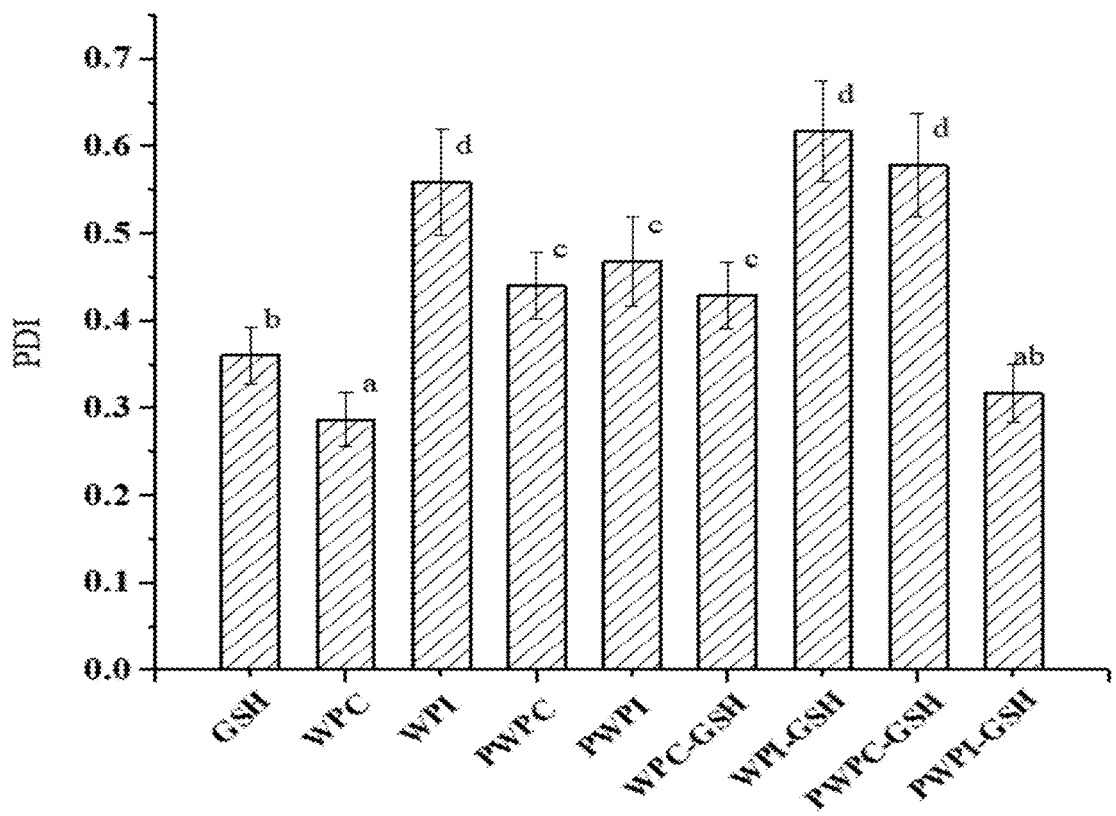
FIG. 14 depicts polydispersity index (PDI) of whey protein encapsulated glutathione nanoparticles, for example, PWPI-GSH, based on WPC and WPI starting materials. Letters a-c meaning significant ($P \leq 0.05$).

FIG. 14 shows polydispersity index (PDI) of whey protein encapsulated glutathione nanoparticles for both WPC and WPI starting materials.

Figure 15:
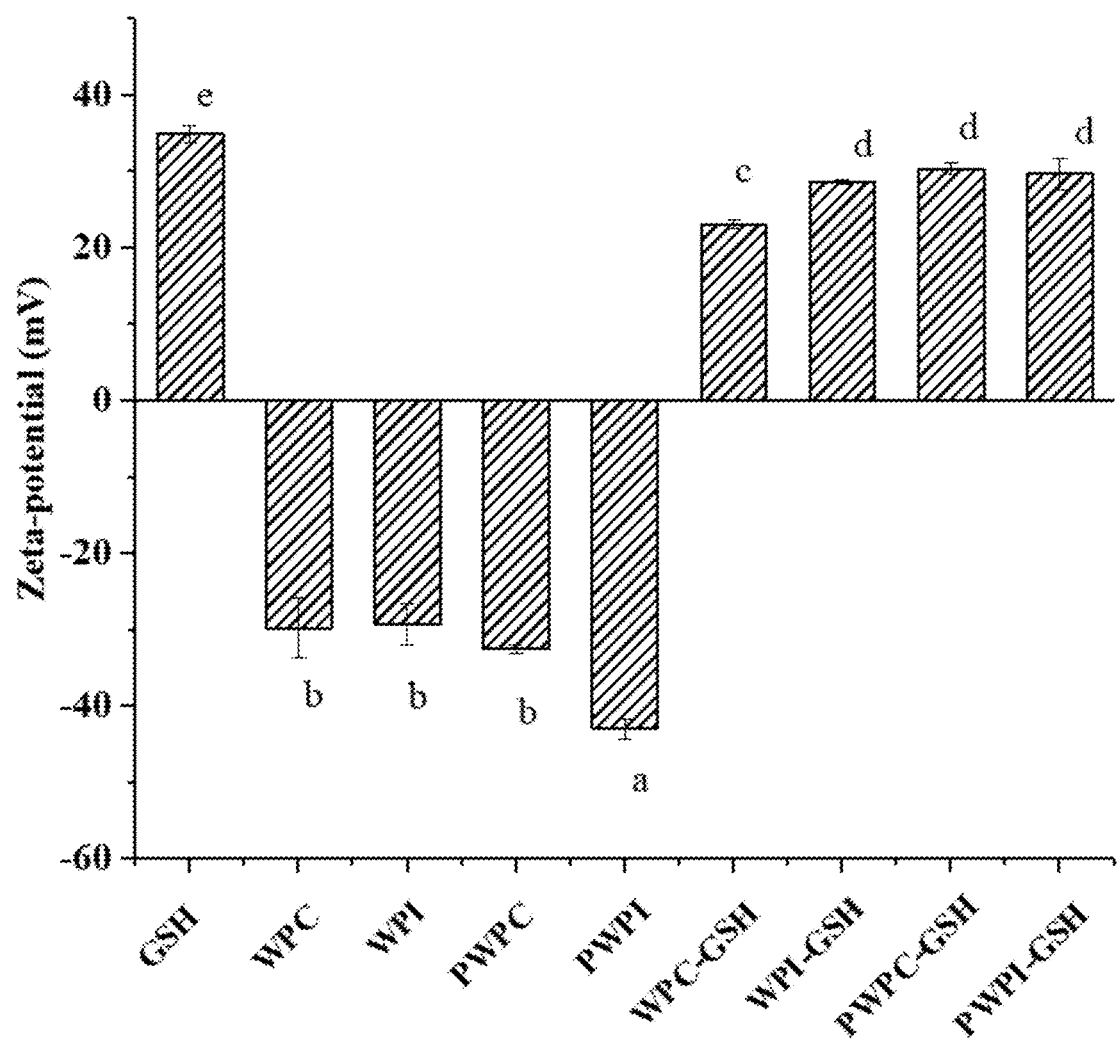
FIG. 15 depicts Zeta potential (mV) of whey protein encapsulated glutathione nanoparticles, for example, PWPI-GSH, based on WPC and WPI starting materials. Letters a-d meaning significant ($P \leq 0.05$).

FIG. 15 shows measured Zeta potential (mV) of whey protein encapsulated glutathione nanoparticles for both WPC and WPI starting materials.

Figure 16A:
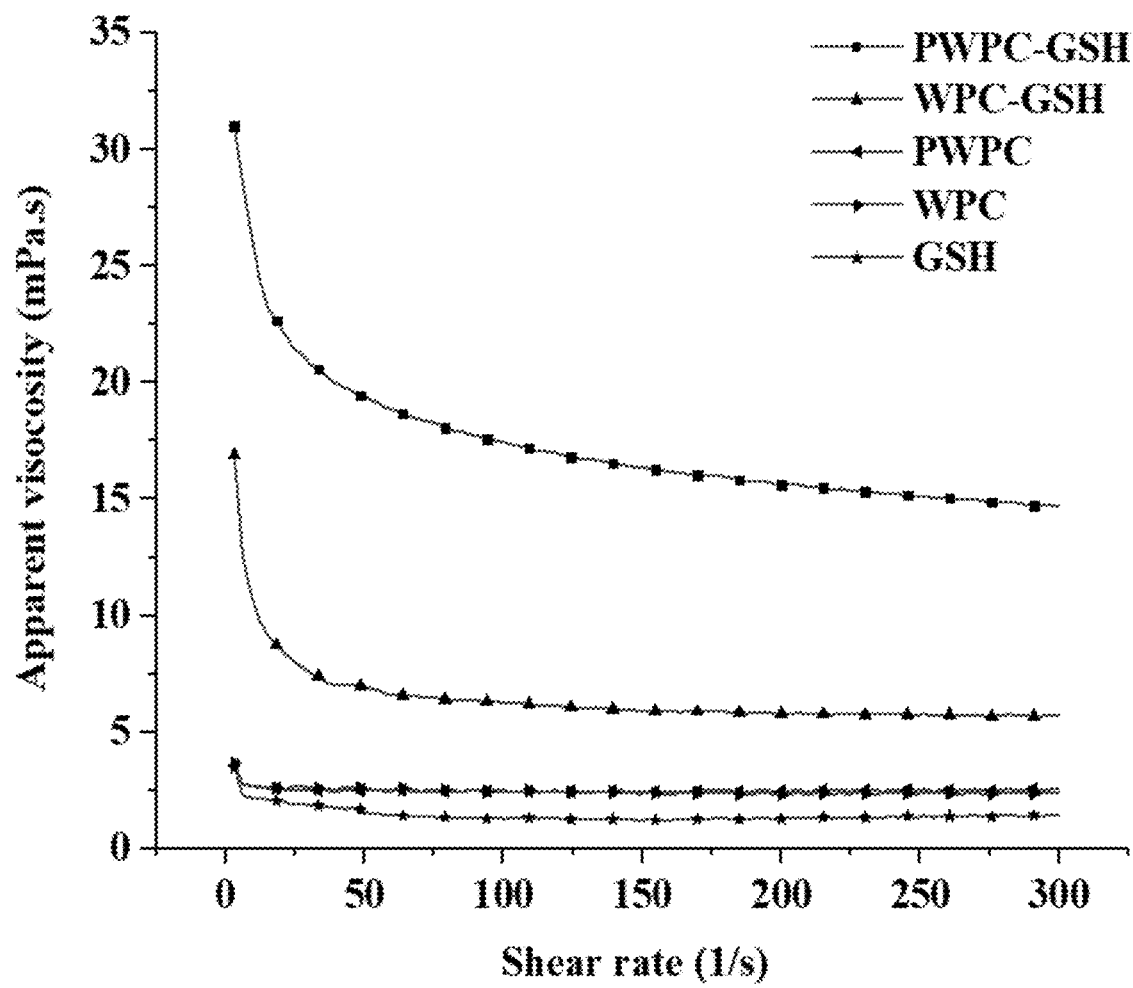
FIG. 16A depicts Apparent viscosity (mPa-sec) vs. Shear rate (1/s) of whey protein encapsulated glutathione nanoparticles, for example, PWPC-GSH, based on WPC.
Figure 16B:
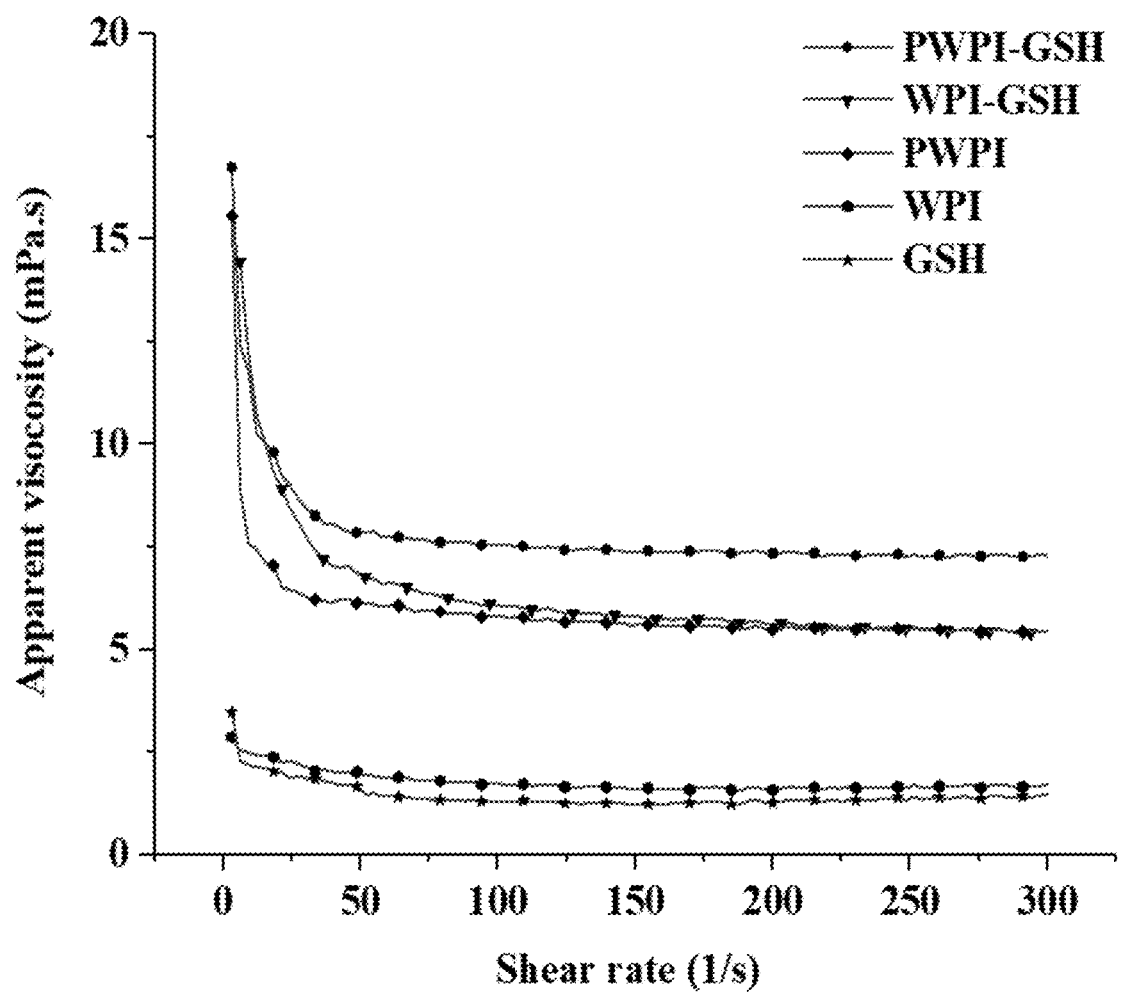
FIG. 16B depicts Apparent viscosity (mPa-sec) vs. Shear rate (1/s) of whey protein encapsulated glutathione nanoparticles, for example, PWPI-GSH, based on WPI.

FIGS. 16A and 16B show apparent viscosity and shear rate relationships of whey protein encapsulated glutathione nanoparticles for WPC and WPI starting materials, respectively.

Figure 17A:
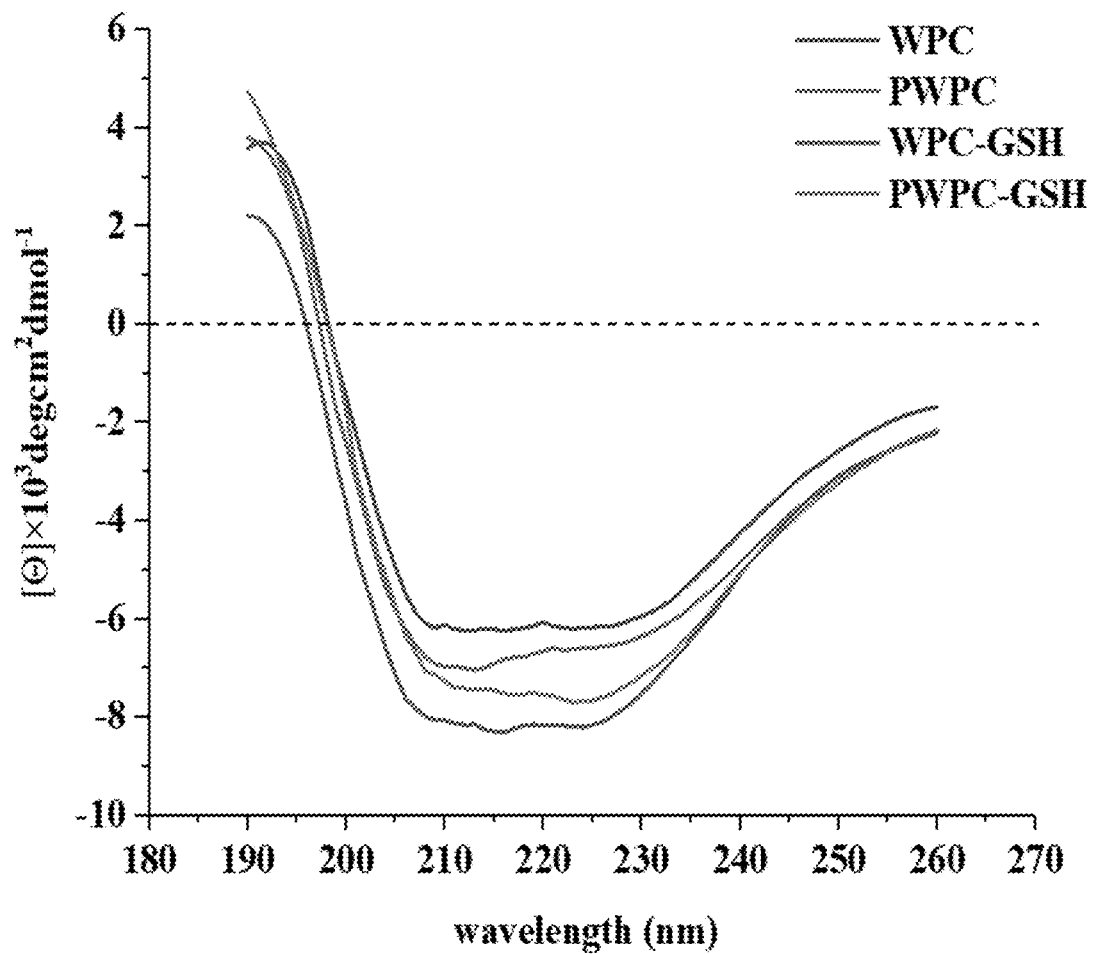
FIG. 17A depicts Circular dichroism $[\Theta] \times 10^3$ deg cm$^2$ dmol$^{-1}$ vs. wavelength (nm) of whey protein encapsulated glutathione nanoparticles, for example, PWPC-GSH, based on WPC.
Figure 17B:
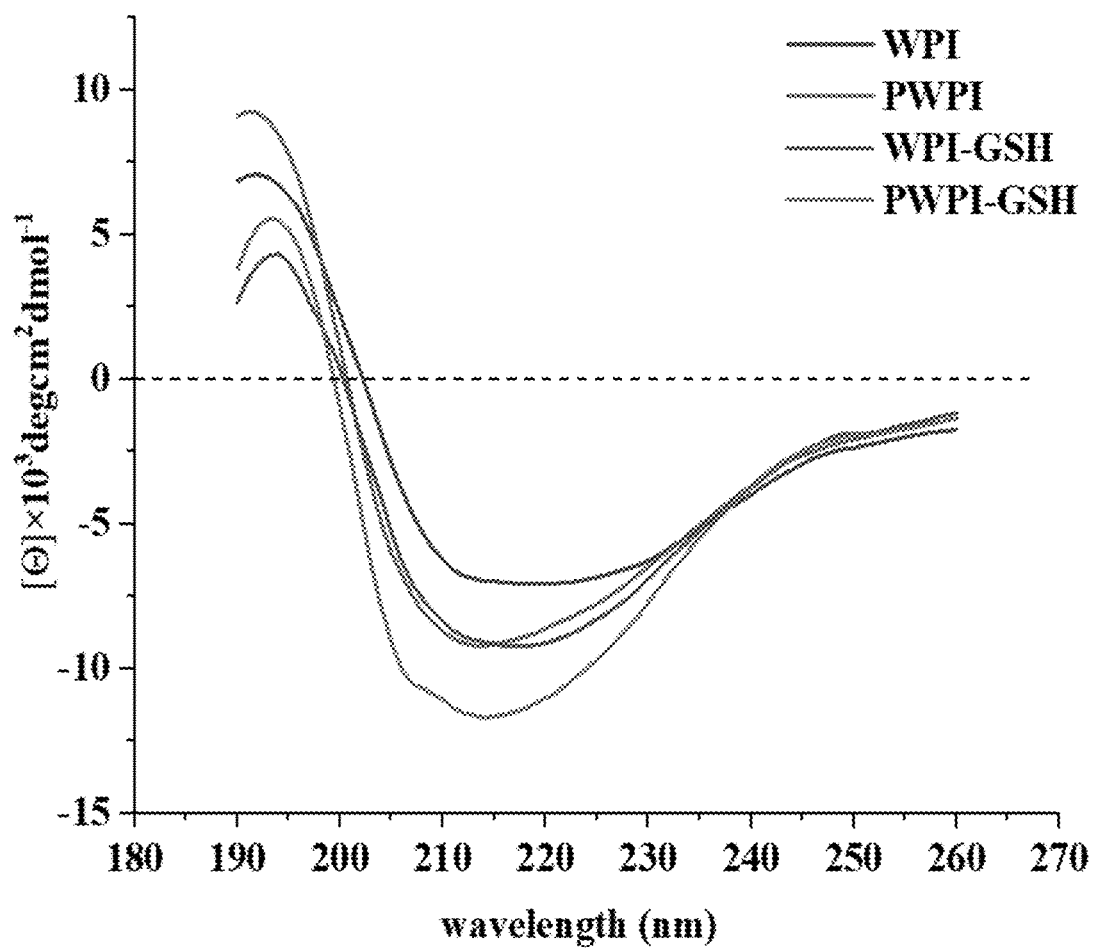
FIG. 17B depicts Circular dichroism $[\Theta] \times 10^3$ deg cm$^2$ dmol$^{-1}$ vs. wavelength (nm) of whey protein encapsulated glutathione nanoparticles, for example, PWPI-GSH, based on WPI.

FIGS. 17A and 17B show circular dichroism of whey protein encapsulated glutathione nanoparticles for WPC and WPI starting materials, respectively.

Figure 18A:
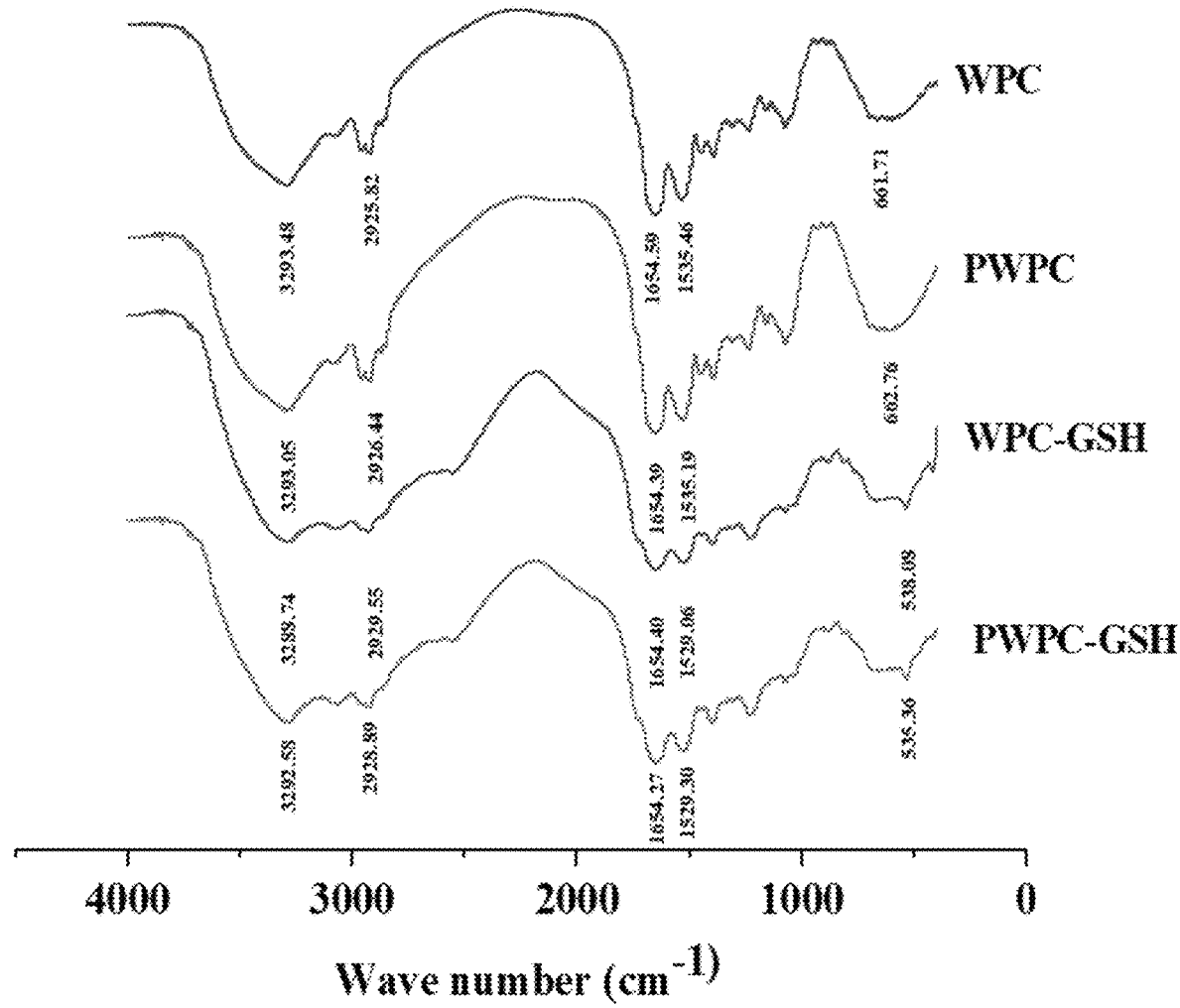
FIG. 18A depicts FT-IR spectra of whey protein encapsulated glutathione nanoparticles, for example, PWPC-GSH, based on WPC, obtained using standard techniques.
Figure 18B:
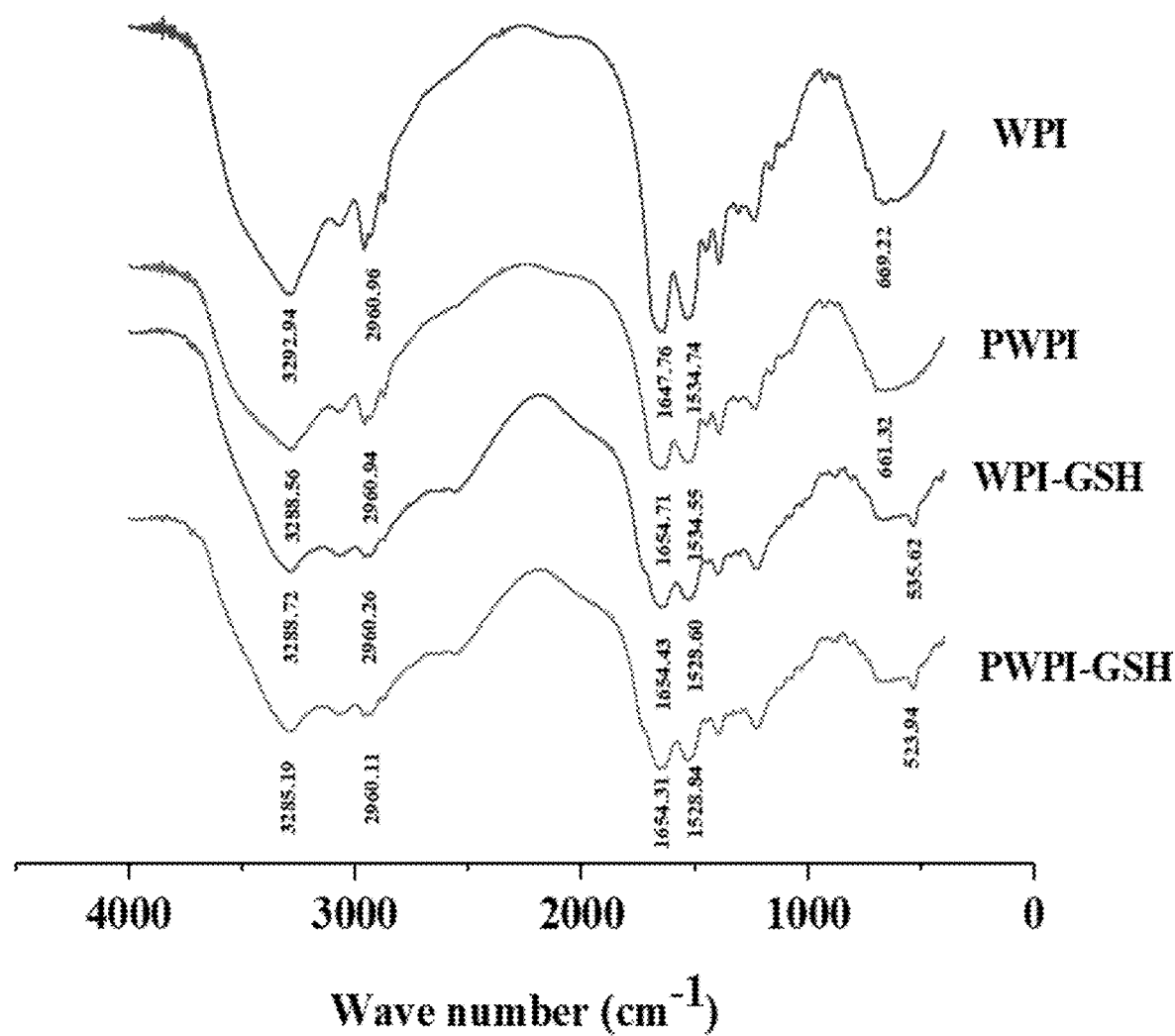
FIG. 18B depicts FT-IR spectra of whey protein encapsulated glutathione nanoparticles, for example, PWPI-GSH, based on WPI, obtained using standard techniques.

FIGS. 18A and 18B show FT-IR spectra of whey protein encapsulated glutathione nanoparticles for WPC and WPI starting materials, respectively.

Example 5

Preparation of PWP-DIM. The procedure of Khan, et al. (2019) was modified as follows.

Components are added to a continuous scratch type stirred, temperature- and pH-controlled tank, or equivalent continuous stirred-type reactor (CSTR) system. Specifically, the tank is jacketed and connecting to a steam source. The temperature is controlled by a thermocouple. The other parts include a pH probe on the side and thermometer at the bottom, along with a mechanical stirring system.

The whey protein was dispersed and polymerized in the tank before DIM was added.

The temperature is ranged from 70 to 95° C., and pH range is from 6.5-9.0.

The measured values of viscosity for the mix of the materials before polymerization and after are 100-300 mPas to 3000 mPas, respectively.

Results and Discussion.

DIM and whey protein concentrate are opposite in terms of hydrophobicity/hydration properties. This process was designed to encapsulate the dispersed phase (DIM) with the polymerized whey protein polymers in the continuous phase. Upon stirring and heating, when the viscosity of the system reaches the desired range, the dispersed phase was suspended and wrapped up by the polymers. The two phases of the materials were formed as a continuous and uniformed micro gel or aggregates.

In the end, the reaction product was spray dried using the standard method and collected as an encapsulated powder.

Example 6

Chemical characterization of PWP-DIM samples. It is well understood that samples made in accordance with the principles of this disclosure may be characterized by various means well known in the art, including, but not limited to, viscosity measurements and other rheological measurements, FT-IR, TEM/SEM photomicrography, microstructure and morphology studies, stability studies (solid phase, solution phase, humidity, thermal), particle size, Zeta potential, and the like. It is expected that the said chemical analyses will further show the unique qualities and properties of the compositions described herein. Cf. Khan, et al., 2019.

Example 7

In a similar manner, polymerized whey protein encapsulated coenzyme-Q10 (PWP-CoQ10) was prepared by the above method using whey protein isolate (WPI) and characterized as an orange flaky powder. Assay (HPLC): 20.69% by weight.

Figure 19:
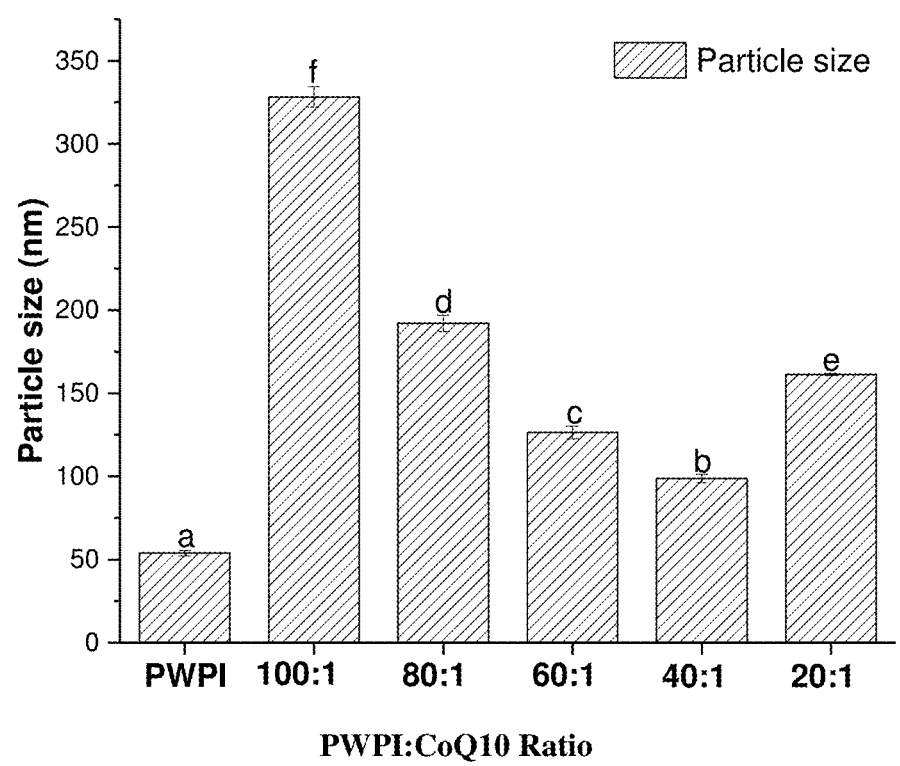
FIG. 19 depicts average particle size (nm) measured by the standard method for PWPI std., PWPI-CoQ10 samples in ratios of 100:1, 80:1, 60:1, 40:1, and 20:1 (PWPI:CoQ10).
Figure 20:
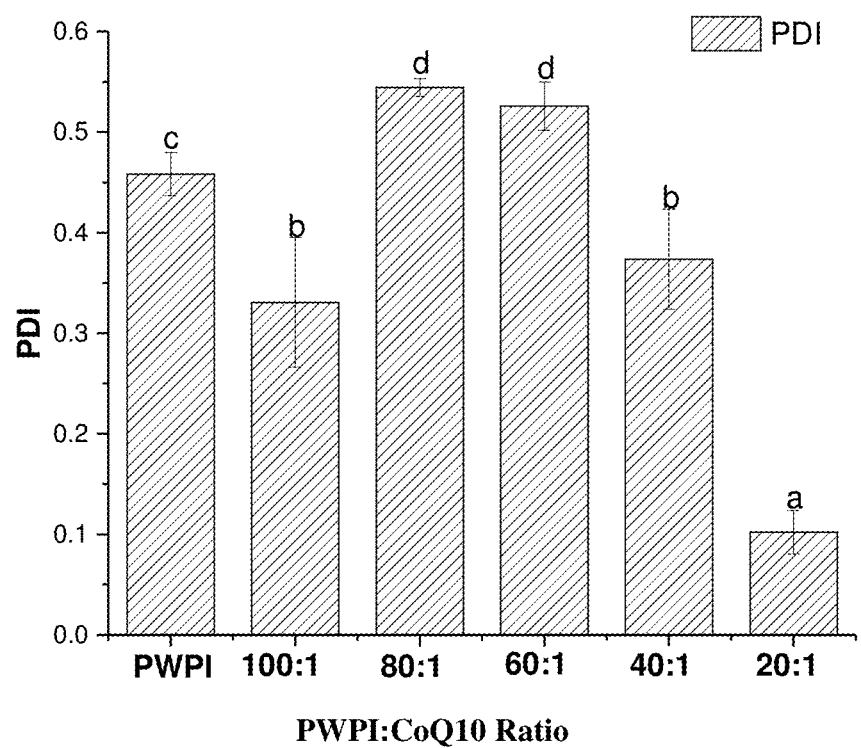
FIG. 20 depicts polydispersity index (PDI) measured by the standard method for PWPI std., PWPI-CoQ10 samples in ratios of 100:1, 80:1, 60:1, 40:1, and 20:1 (PWPI:CoQ10).
Figure 21:
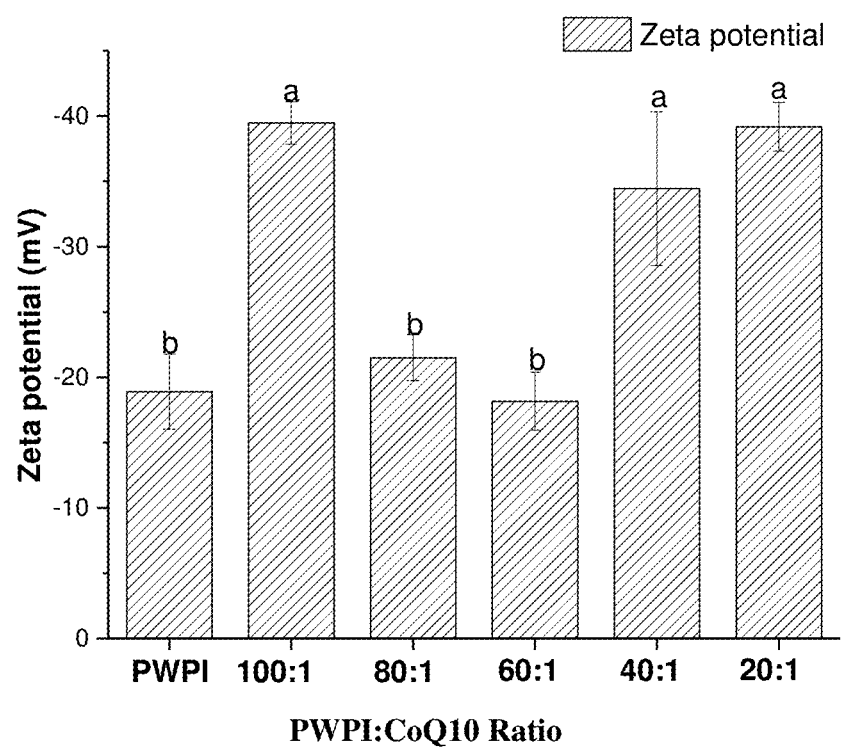
FIG. 21 depicts Zeta potential (mV) measured by the standard method for PWPI std., PWPI-CoQ10 samples in ratios of 100:1, 80:1, 60:1, 40:1, and 20:1 (PWPI:CoQ10).

As shown in FIGS. 19, 20, and 21, the PWP-CoQ10 having various ratios ranging from 20:1 (PWPI:CoQ10) to 100:1 1 (PWPI:CoQ10) was characterized by particle size (nm), polydispersity index (PDI), and Zeta potential (mV), respectively.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments the values may range in value either above or below the stated value in a range of approximately ±5%; in other embodiments the values may range in value either above or below the stated value in a range of approximately ±2%; in other embodiments the values may range in value either above or below the stated value in a range of approximately ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

We claim:
1. A process for making a polymerized whey protein concentrate microencapsulated glutathione, the process comprising the steps of:
    (a) dissolving a powder of whey protein concentrate (WPC) in deionized water at room temperature to provide a WPC aqueous solution, wherein the WPC is present at concentration of 10 w/v %;
    (b) adjusting pH of the WPC aqueous solution to 7-8 and heating said WPC aqueous solution to about 70-80° C. for about 15 minutes;
    (c) cooling the heated WPC aqueous solution to room temperature to provide a polymerized WPC solution;
    (d) adding glutathione powder to the polymerized WPC solution to provide a mixture;
    (e) stirring the mixture to achieve complete dissolution and to provide a clear homogeneous solution; and
    (f) isolating the polymerized WPC microencapsulated glutathione by freeze-drying or spray-drying to provide a powder.
2. The process of claim 1, wherein the and glutathione are used in equal amounts by weight.
3. The process of claim 1, wherein a weight ratio of the WPC to glutathione is from about 1:1 to 1:2.
4. The process of claim 1, wherein the isolating step is spray-drying.
5. The process of claim 1, wherein the isolating step is freeze-drying.

* * * * *

UNITED STATES PATENT AND TRADEMARK OFFICE
CERTIFICATE OF CORRECTION

| | |
|---|---|
| PATENT NO. | : 11,766,407 B2 |
| APPLICATION NO. | : 17/403966 |
| DATED | : September 26, 2023 |
| INVENTOR(S) | : Killpartrick et al. |

Page 1 of 1

It is certified that error appears in the above-identified patent and that said Letters Patent is hereby corrected as shown below:

In the Claims

In Claim 2, Column 22, Line 44, insert after the second instance of the term "the" the term --WPC--.

Signed and Sealed this
Seventh Day of November, 2023

Katherine Kelly Vidal
*Director of the United States Patent and Trademark Office*